United States Patent
Abe et al.

(10) Patent No.: US 9,968,330 B2
(45) Date of Patent: May 15, 2018

(54) ULTRASOUND DIAGNOSTIC APPARATUS, IMAGE PROCESSING APPARATUS, AND IMAGE PROCESSING METHOD

(71) Applicant: Toshiba Medical Systems Corporation, Otawara-shi (JP)

(72) Inventors: Yasuhiko Abe, Otawara (JP); Toshihiko Asanuma, Suita (JP); Satoshi Nakatani, Suita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 870 days.

(21) Appl. No.: 14/499,947

(22) Filed: Sep. 29, 2014

(65) Prior Publication Data

US 2015/0018684 A1 Jan. 15, 2015

Related U.S. Application Data

(63) Continuation of application No. PCT/JP2013/059743, filed on Mar. 29, 2013.

(30) Foreign Application Priority Data

Mar. 30, 2012 (JP) .................................. 2012-082623
Mar. 29, 2013 (JP) .................................. 2013-073762

(51) Int. Cl.
*A61B 8/00* (2006.01)
*A61B 8/08* (2006.01)
(Continued)

(52) U.S. Cl.
CPC ............ *A61B 8/0883* (2013.01); *A61B 8/065* (2013.01); *A61B 8/14* (2013.01); *A61B 8/469* (2013.01);
(Continued)

(58) Field of Classification Search
CPC ....... A61B 8/14; A61B 8/0883; A61B 8/5223; A61B 8/483; A61B 8/469; A61B 8/488; A61B 8/485; A61B 8/065
See application file for complete search history.

(56) References Cited

U.S. PATENT DOCUMENTS 8,540,636 B2 * 9/2013 Kawagishi ............... A61B 8/14
382/128
2006/0122512 A1 6/2006 Abe
(Continued)

FOREIGN PATENT DOCUMENTS

JP 2005-342006 A 12/2005
JP 2006-153867 A 6/2006
(Continued)

OTHER PUBLICATIONS

International Search Report dated Apr. 23, 2013 for PCT/JP2013/059743 dated Mar. 29, 2013 with English Translation.
(Continued)

*Primary Examiner* — Joel Lamprecht
(74) *Attorney, Agent, or Firm* — Oblon, McClelland, Maier & Neustadt, L.L.P.

(57) ABSTRACT

An ultrasound diagnostic apparatus according to an embodiment includes an image acquirer, a volume information calculator, a wall motion information calculator, a time change rate calculator, an extremum detector, and an index calculator. The image acquirer acquires ultrasonic image data including data for a left ventricle. The volume information calculator calculates time-series data of volume information of the left ventricle. The wall motion information calculator calculates time-series data of wall motion information of the left ventricle. The time change rate calculator calculates time-series data of the time change rate of volume information (first time-series data) and time-series data of the time change rate of wall motion information (second time-series data). The extremum detector detects extremums in early diastole of the first time-series data and the second time-series data (first extremum and
(Continued)

second extremum). The index calculator calculates an index using the first extremum and the second extremum.

20 Claims, 13 Drawing Sheets

(51) Int. Cl.
*A61B 8/06* (2006.01)
*A61B 8/14* (2006.01)

(52) U.S. Cl.
CPC .............. *A61B 8/483* (2013.01); *A61B 8/485* (2013.01); *A61B 8/488* (2013.01); *A61B 8/5223* (2013.01)

(56) References Cited

U.S. PATENT DOCUMENTS

| | | |
|---|---|---|
| 2009/0043200 A1 | 2/2009 | Abe |
| 2010/0198072 A1 | 8/2010 | Abe et al. |
| 2011/0190634 A1 | 8/2011 | Kawagishi et al. |
| 2012/0065530 A1 | 3/2012 | Masumoto |
| 2012/0165674 A1 | 6/2012 | Abe et al. |

FOREIGN PATENT DOCUMENTS

| | | |
|---|---|---|
| JP | 2009-039429 A | 2/2009 |
| JP | 2010-194299 A | 9/2010 |
| JP | 2011-177495 A | 9/2011 |
| JP | 2012-055483 A | 3/2012 |
| JP | 2012-061028 A | 3/2012 |

OTHER PUBLICATIONS

International Written Opinion dated Apr. 23, 2013 for PCT/JP2013/059743 dated Mar. 29, 2013.

* cited by examiner dQ/de' BY AREA CHANGE RATE y=3.37x+19.60
$R^2$=0.83

FIRST FRAME

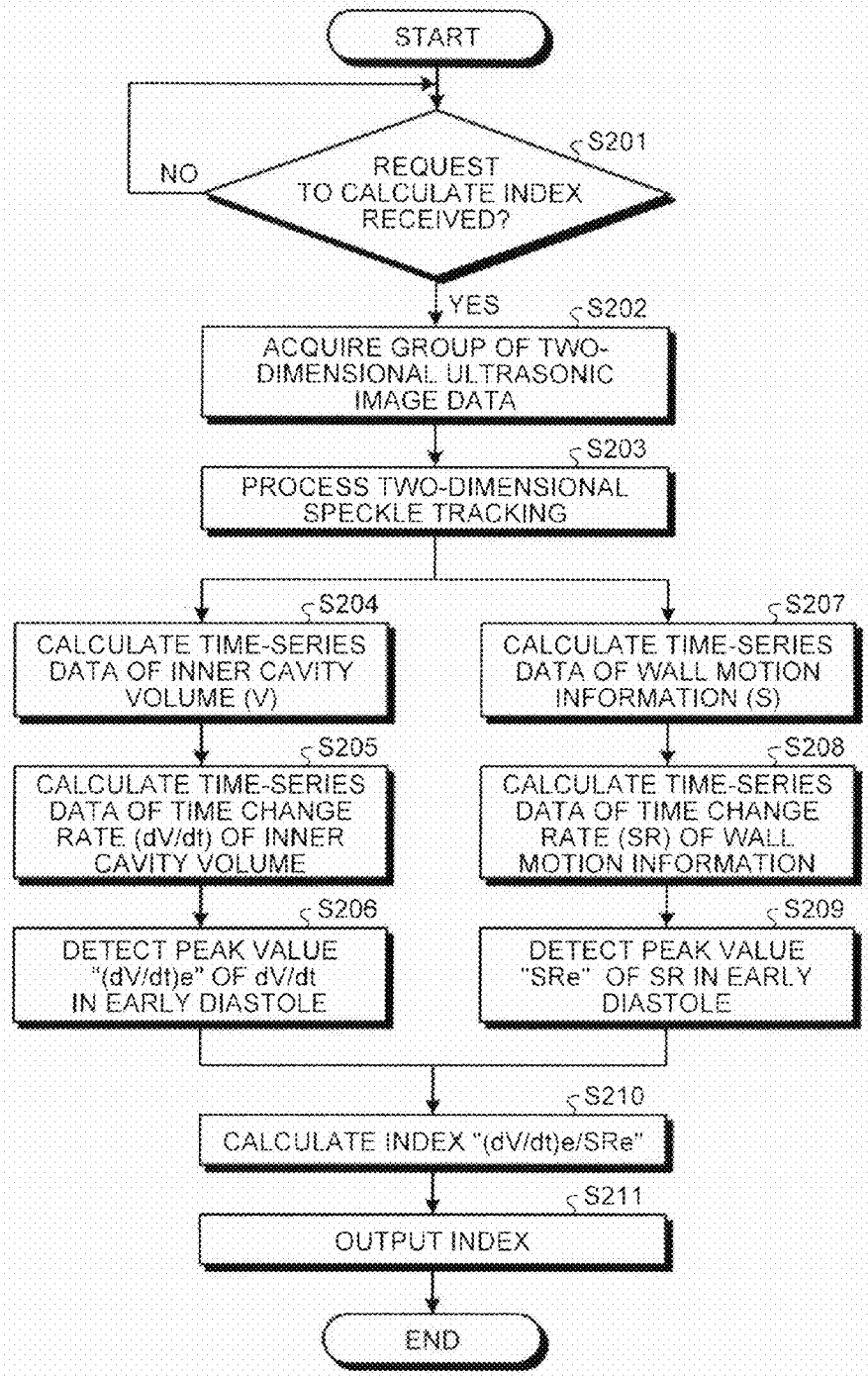

ULTRASOUND DIAGNOSTIC APPARATUS, IMAGE PROCESSING APPARATUS, AND IMAGE PROCESSING METHOD

CROSS-REFERENCE TO RELATED APPLICATION(S)

This application is a continuation of PCT international application Ser. No. PCT/JP2013/059743 filed on Mar. 29, 2013 which designates the United States, incorporated herein by reference, and which claims the benefit of priority from Japanese Patent Application No. 2012-082623, filed on Mar. 30, 2012 and Japanese Patent Application No. 2013-073762, filed on Mar. 29, 2013, the entire contents of which are incorporated herein by reference.

FIELD

Embodiments described herein relate generally to an ultrasound diagnostic apparatus, an image processing apparatus, and an image processing method.

BACKGROUND

An ultrasound diagnostic apparatus can generate an ultrasonic image representing information on the inside of a biological body in a non-invasive manner and display the image thus generated substantially in real time. In diagnoses of cardiac diseases, ultrasound diagnostic apparatuses are used for quantitatively assessing wall motion information of the heart in echocardiography.

Left ventricular end diastolic pressure (LVEDP) is an important index used for diagnoses of cardiac diseases. LVEDP is an index reflecting the left ventricular diastolic function (specifically, compliance of the left ventricle) of a heart and is an important diagnostic index in diagnoses and treatments of cardiac diseases. For example, it is known that a heart with high LVEDP has a poor prognosis. To measure LVEDP accurately, invasive cardiac catheter tests are required, which are not usually used in clinical practices.

In clinical practices, "E/e'" that can be measured by non-invasive method in echocardiography is used as an index for estimating LVEDP. "E/e'" is widely known as an index correlating with left ventricular filling pressure and LVEDP, and can be measured using the pulsed wave (PW) Doppler method. "E" corresponds to the wave height at early diastole in a waveform of left ventricular inflow velocities plotted along the cardiac time phase (wave height of E-waves). Measurement of "E", for example, is performed by setting a range gate at the mitral orifice and collecting blood flow PW Doppler waveforms. "e'" corresponds to the wave height at early diastole in a waveform of mitral annulus tissue velocities plotted along the cardiac time phase. Measurement of "e'", for example, is performed by setting a range gate at the mitral annulus and collecting tissue PW Doppler waveforms. "E/e'" is calculated as the ratio between "E" and "e'".

To calculate "E/e'", both left ventricular inflow blood velocities and mitral annulus tissue velocities need to be measured. "E" and "e'" have conventionally been measured from different heart beats. There are cases, however, where "E/e'" calculated using "E" and "e'" measured from different heart beats shows low accuracy. For the reason described above, in recent years, measurement of "E" and "e'" has been simultaneously performed from the same heart beat using a technique with which Doppler waveforms in two regions can be simultaneously collected by performing PW Doppler scanning on a time sharing basis. With this technique, however, "E/e'" is not always an index accurately reflecting the LVEDP.

BRIEF DESCRIPTION OF THE DRAWINGS

FIG. 14 is a flowchart illustrating an example of processing performed by an ultrasound diagnostic apparatus according to the second embodiment;

DETAILED DESCRIPTION

An ultrasound diagnostic apparatus according to the present embodiments includes an image acquirer, a volume information calculator, a wall motion calculator, a time charge rate calculator, an extremum detector, and an index calculator. The image acquirer is configured to acquire a group of ultrasonic image data generated by ultrasonic scanning on a heart including at least a left ventricle for a period of one or more heart beats. The volume information calculator is configured to calculate, from the group of the ultrasonic image data, time-series data of volume information in a first region of interest in the left ventricle. The wall motion information calculator configured to calculate, from the group of the ultrasonic image data, time-series data of wall motion information in a second region of interest in the left ventricle. The time change rate calculator is configured to calculate, from the time-series data of the volume information, first time-series data that is time-series data of a time change rate of volume information and calculate, from the time-series data of the wall motion information, second time-series data that is time-series data of a time change rate of wall motion information. The extremum detector is configured to detect an extremum in early diastole of the first time-series data as a first extremum and detect an extremum in early diastole of the second time-series data as a second extremum. The index calculator is configured to calculate an index using the first extremum and the second extremum.

An ultrasound diagnostic apparatus according to embodiments will be explained in detail below with reference to accompanying drawings.

First Embodiment

Figure 1:
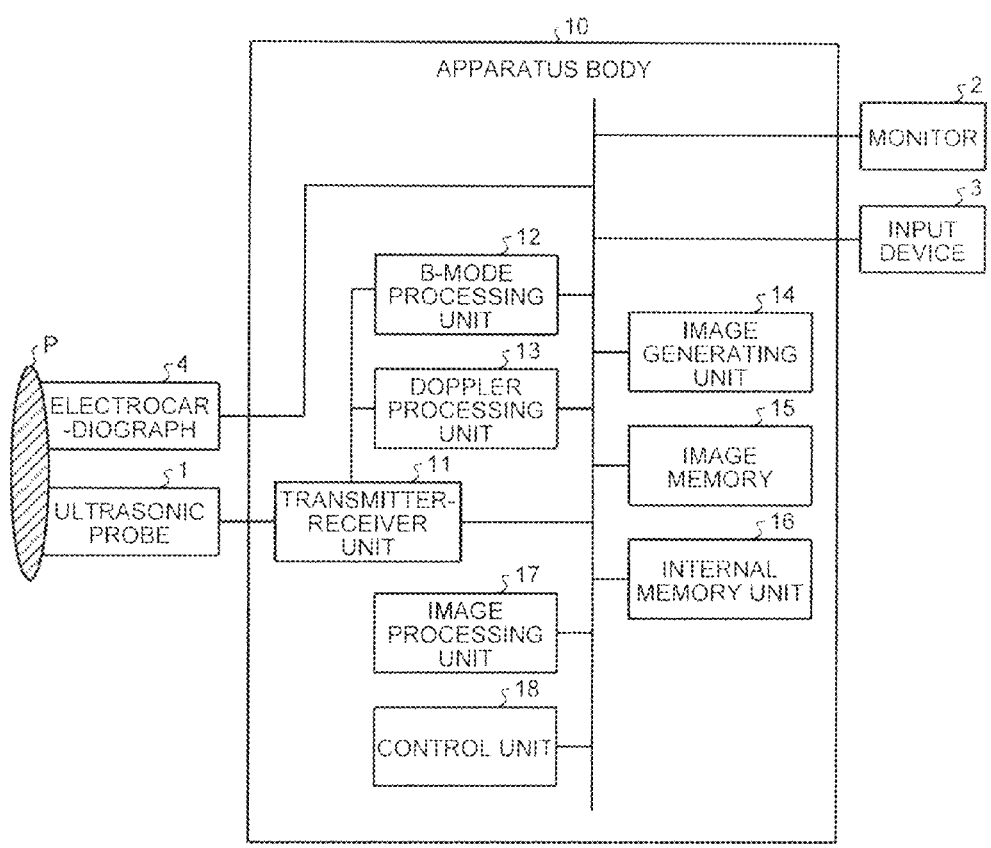
FIG. 1 is a block diagram illustrating a configuration example of an ultrasound diagnostic apparatus according to a first embodiment.

The configuration of an ultrasound diagnostic apparatus according to a first embodiment will be first described. FIG. 1 is a block diagram illustrating a configuration example of the ultrasound diagnostic apparatus according to the first embodiment. As illustrated in FIG. 1, the ultrasound diagnostic apparatus according to the first embodiment includes an ultrasonic probe 1, a monitor 2, an input device 3, an electrocardiograph 4, and an apparatus body 10.

The ultrasonic probe 1 includes a plurality of piezoelectric transducer elements. The piezoelectric transducer elements generate ultrasonic waves based on a drive signal supplied from a transmitter-receiver unit 11 included in the apparatus body 10 described later. The ultrasonic probe 1 receives a reflected wave from a subject P to convert the reflected wave thus received into an electric signal. The ultrasonic probe 1 also includes matching layers provided to the piezoelectric transducer elements and backing materials and so on preventing ultrasonic waves from traveling backwards from the piezoelectric transducer elements. The ultrasonic probe 1 is removably attached to the apparatus body 10.

When ultrasonic waves are transmitted from the ultrasonic probe 1 to the subject P, the ultrasonic waves thus transmitted are sequentially reflected on the planes of discontinuity of acoustic impedances in body tissues of the subject P and then received by the plurality of piezoelectric transducer elements included in the ultrasonic probe 1 as reflected wave signals. The amplitudes of the reflected wave signals thus received depend on the differences between the acoustic impedances on a plane of discontinuity on which the ultrasonic waves are reflected. When the ultrasonic pulses transmitted are reflected on a moving blood flow or the surface of a cardiac wall, for example, the reflected wake signals undergoes a frequency shift depending on the velocity component in the ultrasound transmission direction of the moving body because of the Doppler effect.

The ultrasonic probe 1 according to the first embodiment is an ultrasonic probe that can scan the subject P three-dimensionally as well as two-dimensionally using ultrasonic waves. Specifically, the ultrasonic probe 1 according to the present embodiment is a mechanical four-dimensional probe that two-dimensionally scans the subject P with a plurality of piezoelectric transducer elements disposed in line and also three-dimensionally scans the subject P by oscillating the piezoelectric transducer elements at a predetermined angle (oscillation angle). Alternatively, the ultrasonic probe 1 according to the first embodiment is a two-dimensional matrix array probe that can perform three-dimensional ultrasonic scanning on the subject P with the plurality of piezoelectric transducer elements disposed in a matrix shape. The two-dimensional matrix array probe can also two-dimensionally scan the subject P by converging ultrasonic waves and transmitting the ultrasonic waves thus converted.

The input device 3 includes a mouse, a keyboard, buttons, a panel switch, a touch command screen, a foot switch, a track ball, or a joystick, and receives various setting requests from the operator of the ultrasound diagnostic apparatus and transmits the setting requests thus received to the apparatus body 10. The setting information that the input device 3 according to the first embodiment receives from the operator will be described later.

The monitor 2 displays a graphical user interface (GUI) through which the operator of the ultrasound diagnostic apparatus inputs various setting requests using the input device 3 and displays ultrasonic images generated by the apparatus body 10, for example.

The electrocardiograph 4 acquires electrocardiogram (ECG) of the subject P as a biological signal of the subject P three-dimensionally scanned. The electrocardiograph 4 transmits the electrocardiogram thus acquired to the apparatus body 10.

The apparatus body 10 is an apparatus that generates ultrasonic image data based on the reflected wave signal received by the ultrasonic probe 1. The apparatus body 10 illustrated in FIG. 1 is an apparatus that can generate two-dimensional ultrasonic image data based on two-dimensional reflected wave signal data received by the ultrasonic probe 1. The apparatus body 10 illustrated in FIG. 1 also is an apparatus that can generate three-dimensional ultrasonic image data based on three-dimensional reflected wave data received by the ultrasonic probe 1. The three-dimensional ultrasonic image data may be referred to as "volume data" in some cases below.

The apparatus body 10 includes a transmitter-receiver unit 11, a B-mode processing unit 12, a Doppler processing unit 13, an image generating unit 14, and an image memory 15, an internal memory unit 16, an image processing unit 17, and a control unit 18 as illustrated in FIG. 1.

The transmitter-receiver unit 11 includes a purse generator, a transmission delay unit, and a pulsar, and supplies a drive signal to the ultrasonic probe 1. The pulse generator repeatedly generates a rate pulse for forming a transmitting ultrasonic wave at a predefined rate frequency. The transmission delay unit provides each rate pulse generated by the pulse generator with a transmission delay time for each piezoelectric transducer element. The transmission delay time is required to focus ultrasonic waves generated by the ultrasonic probe 1 into a beam and to determine transmission directionality. The pulsar applies a drive signal (drive pulse) to the ultrasonic probe 1 at the timing based on the rate pulse. In other words, the transmission delay unit adjusts the transmission direction of ultrasonic waves transmitted from the surface of the piezoelectric transducer elements as required by changing the transmission delay time provided to each rate pulse.

The transmitter-receiver unit 11 has functions capable of instantaneously changing transmission frequencies, transmission drive voltages, and the like in order to perform a predefined scan sequence based on an instruction from the control unit 18 described later. In particular, the transmission drive voltages can be changed with a linear amplifier type of transmission circuit capable of instantaneously changing values or a mechanism electrically switching over a plurality of power source units.

The transmitter-receiver unit 11 includes a preamplifier, an analog/digital (A/D) converter, and a reception delay unit, and an adder, performs various types of processing on the reflected wave signals received by the ultrasonic probe 1, and generates reflected wave data. The preamplifier amplifies the reflected wave signals for each channel. The A/D converter A/D-converts the reflected wave signals thus amplified. The reception delay unit provides a reception delay time required to determine reception directionality. The adder performs addition processing on the reflected wave signals processed by the reception delay unit, and generates reflected wave data. The addition processing performed by the adder enhances reflection components along the direction in accordance with the reception directionality of the reflected wave signals. The transmission and reception directionalities form an integrated reception beam of ultrasound transmission and reception.

The transmitter-receiver unit 11 causes the ultrasonic probe 1 to transmit two-dimensional ultrasonic beams when the subject P is two-dimensionally scanned. The transmitter-receiver unit 11 then generates two-dimensional reflected wave data from two-dimensional reflected wave signals received by the ultrasonic probe 1. The transmitter-receiver unit 11 also causes the ultrasonic probe 1 to transmit three-dimensional ultrasonic beams when the subject P is three-dimensionally scanned. The transmitter-receiver unit 11 then generates three-dimensional reflected wave data from three-dimensional reflected wave signals received by the ultrasonic probe 1.

Various forms are selectable such as cases where the signals output from the transmitter-receiver unit 11 are signals including phase information called radio frequency (RF) signals or signals including amplitude information after envelope demodulation processing, for example.

The B-mode processing unit 12 receives reflected wave signals from the transmitter-receiver unit 11, performs logarithmic amplification, envelope demodulation, and the like, and generates data in which the intensity of a signal is represented by the brightness of its luminance (B-mode data).

The Doppler processing unit 13 performs frequency analysis of velocity information from the reflected wave data received from the transmitter-receiver unit 11 and extracts a blood flow component, a tissue component, and a contrast agent echo component affected by the Doppler effect, thereby generating data (Doppler data) in which moving body information such as velocity, variance, power, and the like are extracted at multiple points.

The B-mode processing unit 12 and the Doppler processing unit 13 according to the first embodiment can process both two-dimensional reflected wave data and three-dimensional reflected wave data. Specifically, the B-mode processing unit 12 generates two-dimensional B-mode data from two-dimensional reflected wave data and three-dimensional B-mode data from three-dimensional reflected wave data. The Doppler processing unit 13 generates two-dimensional Doppler data from two-dimensional reflected wave data and three-dimensional Doppler data from three-dimensional reflected wave data.

The image generating unit 14 generates ultrasonic wave image data from the data generated by the B-mode processing unit 12 and the Doppler processing unit 13. Specifically, the image generating unit 14 generates two-dimensional B-mode image data in which the intensity of a reflected wave signal is represented by the luminance from the two-dimensional B-mode data generated by the B-mode processing unit 12. The image generating unit 14 also generates two-dimensional Doppler image data representing moving body information from the two-dimensional Doppler data generated by the Doppler processing unit 13. The two-dimensional Doppler image data includes a speed image, a variance image, a power image, and an image in which these images are combined. The image generating unit 14 can also generate a Doppler waveform in which speed information of blood flows and tissues are plotted in a time-serial manner from the Doppler data generated by the Doppler processing unit 13.

The image generating unit 14 typically generates ultrasonic image data for display through conversion (scan-conversion) of signal arrays of ultrasonic scan lines into signal arrays of scan lines in a video format represented by television. Specifically, the image generating unit 14 generates ultrasonic image data for display through coordinate conversion in accordance with the form of the ultrasonic scan performed by the ultrasonic probe 1. The image generating unit 14 also performs various types of image processing other than the scan conversion. For example, the image generating unit 14 uses a plurality of image frames after the scan conversion and performs image processing reproducing an image having an average brightness (smoothing processing) and image processing using a differentiation filter in an image (edge enhancement processing). The image generating unit 14 also combines text information on various parameters, scales, body marks, and the like with ultrasonic image data.

Specifically, the B-mode data and the Doppler data are ultrasonic image data before the scan conversion, and data generated by the image generating unit 14 is ultrasonic image data for display after the scan conversion. The B-mode data and the Doppler data are also referred to as raw data.

The image generating unit 14 further generates three-dimensional B-mode image data by performing coordinate conversion on the three-dimensional B-mode data generated by the B-mode processing unit 12. The image generating unit 14 also generates three-dimensional Doppler image data by performing coordinate conversion on the three-dimensional Doppler data generated by the Doppler processing unit 13. In other words, the image generating unit 14 generates "three-dimensional B-mode image data and three-dimensional Doppler image data" as "three-dimensional ultrasonic image data (volume data)".

The image generating unit 14 further performs rendering processing on volume data to generate various types of two-dimensional image data so that the monitor 2 displays the volume data. The rendering processing performed by the image generating unit 14 includes processing performing multi-planer reconstruction (MPR) and generating MPR image data from volume data. The rendering processing performed by the image generating unit 14 also includes processing performing curved MPR on volume data and processing performing maximum intensity projection on volume data. The rendering processing performed by the image generating unit 14 further includes volume rendering (VR) processing generating two-dimensional image data on which three-dimensional information is reflected.

The image memory 15 is a memory storing therein image data for display generated by the image generating unit 14. The image memory 15 can also store therein data generated by the B-mode processing unit 12 and the Doppler processing unit 13. The B-mode data and the Doppler data stored in the image memory 15 can be called by the operator after diagnosis, for example, and serve as ultrasonic image data for display via the image generating unit 14. The image generating unit 14 stores in the image memory 15 volume data and the ultrasonic scanning time required for generating the volume data in association with electrocardiographic waveforms transmitted from the electrocardiograph 4. The image processing unit 17 and the control unit 18 described later can refer to the data stored in the image memory 15, thereby acquiring the cardiac time phase at the time of ultrasonic scanning performed for generating the volume data.

The internal memory unit 16 stores therein various types of data such as control programs for performing transmission and reception of ultrasonic waves, image processing, and display processing; diagnostic information (patients' IDs and doctors' opinions, for example); a diagnostic protocol; and various body marks. The internal memory unit 16 is also used, for example, for storing the images stored by the image memory 15 as necessary. The data stored in the internal memory unit 16 can be transferred to an external device through an interface (not illustrated). The external device includes a personal computer used by a doctor performing image diagnosis, a storage medium such as a CD or DVD, and a printer.

The image processing unit 17 is installed in the apparatus body 10 to perform computer aided diagnosis (CAD). The image processing unit 17 acquires ultrasonic image data stored in the image memory 15, thereby performing image processing to support diagnosis. The image processing unit 17 then stores the results from the image processing in the image memory 15 and the internal memory unit 16. The processing performed by the image processing unit 17 will be described later.

The control unit 18 controls the entire processing performed by the ultrasound diagnostic apparatus. Specifically, the control unit 18 controls processing performed by the transmitter-receiver unit 11, the B-mode processing unit 12, the Doppler processing unit 13, the image generating unit 14, and the image processing unit 17 based on various setting requests input by the operator through the input device 3 and various control programs and various types of data read from the internal memory unit 16. The control unit 18 also controls the monitor 2 to display ultrasonic image data for display stored in the image memory 15 and the internal memory unit 16. The control unit 18 further performs control on the results from processing performed by the image processing unit 17 to be displayed on the monitor 2 or output to an external device.

Described above is the overall configuration of the ultrasound diagnostic apparatus according to the first embodiment. Based on the configuration described above, the ultrasound diagnostic apparatus according to the first embodiment calculates an index substituting for "E/e'" used as an index correlating with left ventricular end-diastolic pressure.

As described above, both left ventricular inflow blood velocities and mitral annulus tissue velocities need to be measured to calculate "E/e'" conventionally used as an index correlating with LVEDP. "E" and "e'" have conventionally been measured at different heart beats. Alternatively, to increase accuracy of "E/e'", a technique with which Doppler waveforms in two regions can be simultaneously collected has been used to simultaneously measure "E" and "e'" from the same heart beat. The mitral annulus tissue velocities are measured in one region or in two regions (typically, two regions on the septal and lateral wall in a four-chamber section). To accurately measure the mitral annulus tissue velocities, measurement of the mitral annulus tissue velocities is preferably performed in a plurality of regions for each of a plurality of sections.

However, when "E" and "e'" are simultaneously collected, there is only one region where "e'" can be measured. To obtain "e'" in a plurality of regions, measurement needs to be performed at different heart beats, lengthening the time for image acquisition. When measuring "E" and "e'" at different heart beats, "e'" can be measured in a plurality of, that is, two or more regions, but increasing the measurement regions lengthens the testing time.

In diagnosis of left ventricular diastolic performance, when "E/e'" is below "8", the diastolic performance is considered as normal, and when "E/e'" is over "15", the diastolic performance is considered as abnormal. However, the cutoff value as a judgment criterion between normal and abnormal is not always "15", and a wide range of values between "8" and "22" has been generally used. The causes for the wide overlap of the cutoff values between "8" and "22" are classified roughly into the following two causes.

The first cause is that the results of measurement of "E" and "e'" performed using the Doppler method include errors dependent on the Doppler angles. In particular, when "e'" is measured using the tissue Doppler method, the errors in the measurement results are increased unless the motion direction of the mitral annulus corresponds to the scan line direction. For example, in the case of dilated cardiomyopathy (DCM) with which the left ventricle grows spherical, the motion direction of the mitral annulus may not correspond to the scan line direction, which may increase errors of "e'". To solve this problem, two-dimensional speckle tracking (hereinafter, 2DT) is used in recent years in which an index corresponding to "E/e'" is obtained by using a peak value of the global strain rate in the longitudinal direction in early diastole. Because the speckle tracking methods do not use the Doppler method for detecting motions, the problem of dependency on the Doppler angle is not involved. However, the method described above cannot simultaneously measure "E" and "e'" at one heart beat.

The second cause is that while "E" is an index for global function of the left ventricle, "e'" is an index for a local part of the mitral annulus as described above.

There have been some cases where "E/e'" is not always an index accurately reflecting left ventricular end-diastolic pressure LVEDP as describe above. From this background, the ultrasound diagnostic apparatus according to the first embodiment is configured to calculate an index accurately reflecting a left ventricular end-diastolic pressure LVEDP by means of the function of the image processing unit 17 described below.

Figure 2:
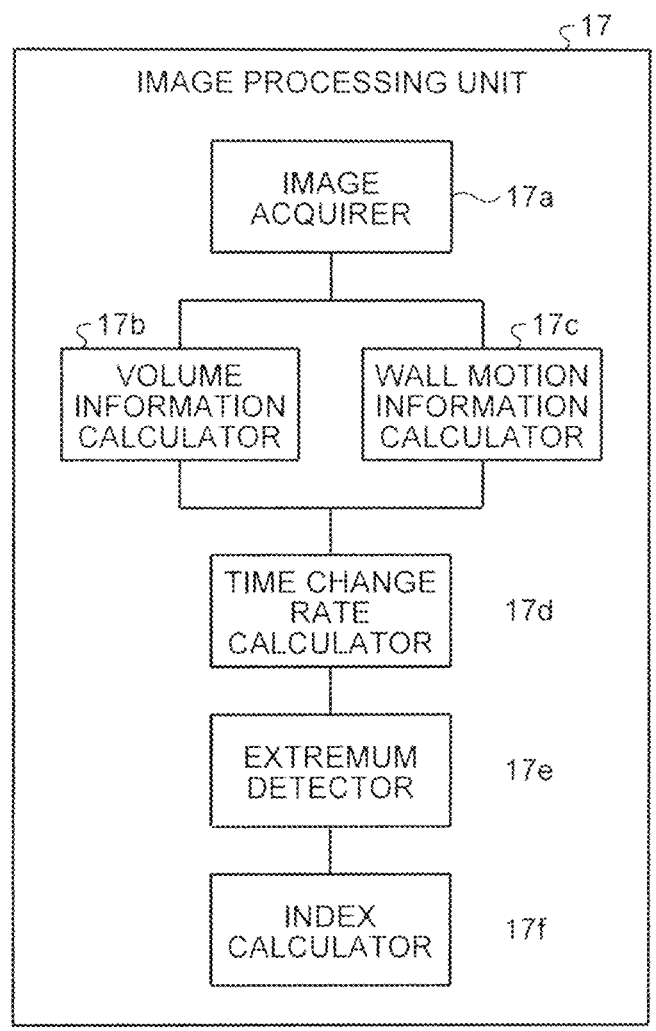
FIG. 2 is a block diagram illustrating a configuration example of an image processing unit according to the first embodiment.

FIG. 2 is a block diagram illustrating a configuration example of an image processing unit according to the first embodiment. As illustrated in FIG. 2, the image processing unit 17 according to the first embodiment includes an image acquirer 17a, a volume information calculator 17b, a wall motion information calculator 17c, a time change rate calculator 17d, an extremum detector 17e, and an index calculator 17f.

According to the first embodiment, the operator first uses the ultrasonic probe 1 that can perform three-dimensional scanning to three-dimensionally scan the left heart of the subject P for the period of one or more heart beats by approaching the cardiac apex, for example. Based on this scanning, the image generating unit 14 generates a plurality of pieces of three-dimensional ultrasonic image data along the time series for the period of one or more heart beats and stores the data thus generated in the image memory 15. The pieces of three-dimensional ultrasonic image data stored in the image memory 15 are a group of three-dimensional ultrasonic image data generated by ultrasonic scanning over the heart including at least the left ventricle for the period of one or more heart beats. The three-dimensional ultrasonic image data according to the first embodiment is three-dimensional B-mode image data.

Figure 3:
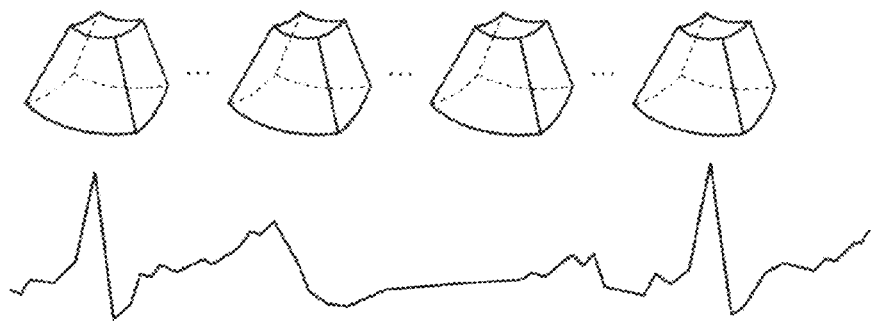
FIG. 3 is a diagram illustrating the image acquirer according to the first embodiment.

Thereafter, the image acquirer 17a acquires the group of three-dimensional ultrasonic image data generated by ultrasonic scanning over the heart including at least left ventricle for the period of one or more heart beats. FIG. 3 is a diagram illustrating the image acquirer according to the first embodiment. The image acquirer 17a acquires a plurality of pieces of three-dimensional ultrasonic image data along the time series for the period of one or more heart beats as illustrated in FIG. 3. Each piece of three-dimensional ultrasonic image data includes left ventricle of the subject P.

Thereafter, the volume information calculator 17b calculates time-series data of volume information in the first region of interest in the left ventricle from the group of three-dimensional ultrasonic image data. The wall motion information calculator 17c calculates time-series data of wall motion information in the second region of interest in the left ventricle from the same group of three-dimensional ultrasonic image data.

Specifically, the volume information calculator 17b uses the results from tracking the position of the first region of interest by means of processing including pattern matching between pieces of image data and calculates volume information. The wall motion information calculator 17c uses the results from tracking the position of the second region of interest by means of processing including pattern matching between pieces of image data and calculates wall motion information.

More specifically, the volume information calculator 17b and the wall motion information calculator 17c use the results from three-dimensional speckle tracking (hereinafter, 3DT) performed on three-dimensional moving image data acquired by the three-dimensional echocardiography and calculate the volume information in the first region of interest and the wall motion information in the second region of interest. The speckle tracking methods are methods for estimating accurate motions by using optical flow methods and various types of spatial-temporal interpolation processing, for example, in combination with the pattern matching processing. The speckle tracking methods also include a method for estimating motions without performing pattern matching processing. Described below is a case where 3DT processing is performed by the volume information calculator 17b. However, according to the first embodiment, both cases are acceptable: a case where the 3DT processing is performed by the image acquirer 17a or the wall motion information calculator 17c and another case where the 3DT processing is performed by a processing unit other than the image processing unit 17 (the control unit 18, for example).

Figure 4:
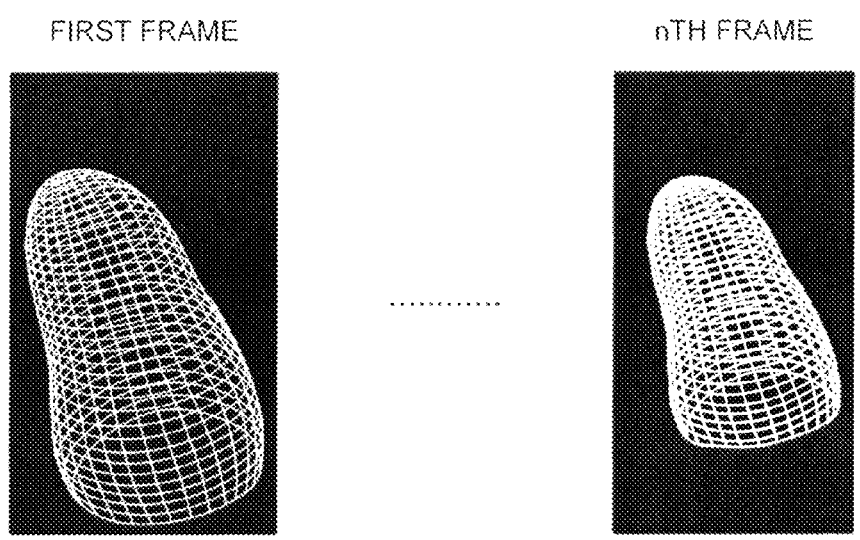
FIG. 4 is a diagram illustrating an example of three-dimensional speckle tracking.

FIG. 4 is a diagram illustrating an example of three-dimensional speckle tracking. For example, the input device 3 receives a request to display the first frame (first volume) of the group of three-dimensional ultrasonic image data from the operator. The control unit 18 to which the request to display is transferred reads out the three-dimensional ultrasonic image data in the first frame from the image memory 15 and directs the monitor 2 to display the data thus read out. For example, the control unit 18 directs the image generating unit 14 to generate a plurality of pieces of MPR image data on which the three-dimensional ultrasonic image data in the first frame is cut along the sections in a plurality of directions and controls the monitor 2 to display the pieces of data thus generated.

Thereafter, the operator refers to the plurality of pieces of MPR image data displayed on the monitor and sets a plurality of tracking points where 3DT is performed. To cite an example, the operator traces the positions of the left ventricular endocardium and the epicardium in each piece of MPR image data. The volume information calculator 17b reconstructs three-dimensional boundary surfaces from the left ventricular endocardial surface and the epicardial surface thus traced. The volume information calculator 17b then sets up a mesh structured by a plurality of rectangles with respect to the endocardial surface in the first frame and sets the top of each rectangle to a tracking point as illustrated in FIG. 4. The volume information calculator 17b also sets up a mesh structured by a plurality of rectangles with respect to the epicardial surface in the first frame and sets the top of each rectangle to a tracking point (not illustrated). At this time, the volume information calculator 17b sets each tracking point on the endocardial surface in a pair with the corresponding tracking point on the epicardial surface. The volume information calculator 17b then sets template data with respect to each of the tracking points set in the first frame The template data consists of a plurality of voxels centering on each of the tracking points.

The volume information calculator 17b then explores a region that fits best to the speckle pattern of the template data between two frames the most, thereby traces to which position the template data moves in the next frame. The volume information calculator 17b thus traces to which position in the nth frame each tracking point in the first frame moves, as illustrated in FIG. 4. It should be noted the mesh for setting the tracking points may be set by the volume information calculator 17b detecting the endocardial surface or the epicardial surface of the left ventricle included in the first frame.

The volume information calculator 17b performs 3DT with respect to the group of three-dimensional ultrasonic image data with the entire left ventricle (the endocardium and the epicardium of the left ventricle, for example) as the first region of interest. The volume information calculator 17b then calculates the inner cavity (V) surrounded by the endocardial surface of the left ventricle from the results of 3DT on the endocardium in each volume data. The volume information calculator 17b thus generates time-series data for the period of one or more heart beats of the inner cavity volume (V). The volume information calculator 17b then generates the volume of the inside of the epicardium from the results of the 3DT of the epicardium. The volume information calculator 17b generates time-series data for the period of one or more heart beats of the volume of the epicardium. In the first embodiment, temporal differential of the inner cavity volume (V) is used as a value corresponding to the left ventricular inflow blood velocity as described later.

The wall motion information calculator 17c generates time-series data for the period of one or more heart beats of the wall motion information from the result of 3DT with respect to the group of three-dimensional ultrasonic image data. In the first embodiment, as described later, the temporal differential of the wall motion information is used as a value corresponding to the mitral annular velocity. Described below is a specific example of the wall motion information calculated from the results of 3DT and the second region of interest.

The wall motion information calculator 17c calculates the wall motion information and strain from the results of 3DT performed on the endocardium and the epicardium. The wall motion information calculator 17c calculates strain in the longitudinal direction (LS) and strain in the circumferential direction (CS), and strain in the radial direction (RS).

Alternatively, the wall motion information calculator 17c calculates area change ratio (AC) of the left ventricle endocardial surface as wall motion information from the results of 3DT performed on the endocardium, for example. From the viewpoint of a value corresponding to the mitral annular velocity, LS is the most suitable for the wall motion information. In the viewpoint of a value corresponding to the change of the inner cavity volume (V), AC is the most suitable for the wall motion information.

Alternatively, the wall motion information calculator 17c may calculate displacement from the results of 3DT performed on the endocardium or the epicardium, for example. The temporal differential of the displacement can also be used as a value corresponding to the mitral annular velocity. When using the displacement as the wall motion information, the wall motion information calculator 17c can calculate displacement in the longitudinal direction (LD) and displacement in the radial direction (RD). The wall motion information calculator 17c may alternatively calculate absolute displacement (AD) of the tracking point in a time phase other than the reference phase with respect to the tracking point in the reference time phase (R-waves, for example).

"Strain", "area change ratio", and "displacement" are wall motion information obtained by using the speckle tracking technique and can trace the motion of the myocardium, enabling their definitions in a local region. "Strain" and "area change ratio" in particular are known to be advantageous to "displacement" in that information on expansion and contraction of a local region of the myocardium can be obtained without affection of "translation", which is the motion of the entire heart.

Both cases are acceptable: a case where the wall motion information calculator 17c calculates wall motion information of the entire left ventricle (overall wall motion information) as wall motion information in the second region and another case where the wall motion information calculator 17c calculates wall motion information of the left ventricle mitral annulus (local wall motion information) as wall motion information in the second region. For example, the wall motion information calculator 17c calculates local wall motion information using segmented regions recommended by the American Society of Echocardiography and American Heart Association.

When the second region of interest is the entire left ventricle, the wall motion information calculator 17c calculates wall motion information in all segmented regions and averages all wall motion information thus calculated, thereby calculating wall motion information of the entire left ventricle.

When the second region of interest is the valve ring region (mitral annular region) of the left ventricle, the wall motion information calculator 17c calculates wall motion information of each of the anterior wall, the side wall, the posterior wall, the inferior wall, the septum, and the anteroseptal wall at the base level and averages the six sets of the wall motion information thus calculated, thereby calculating wall motion information of the valve ring of the left ventricle.

From the viewpoint of a value corresponding to change of the inner cavity volume (V), overall wall motion information such as "the entire endocardial surface" and "the entire valve ring region" is preferably used rather than "local wall motion information in the valve ring region" such as "wall motion information of the anteroseptal wall" and "average of wall motion information of the anteroseptal wall and the side wall". "Wall motion information of the entire valve ring region" is local wall motion information for the left ventricle, but is overall wall motion information for the valve ring.

When LS, CS, RS, or RD is used as wall motion information, for example, the wall motion information calculator 17c calculates an average of values in the local regions for the entire left ventricle. When using AC, the wall motion information calculator 17c calculates an average of a value in the local regions over the entire left ventricle or the area change ratio for the entire endocardial surface. When using LD or AD, the wall motion information calculator 17c preferably calculates an average of the entire valve ring region.

Both cases are acceptable: a case where the information calculated as the wall motion information is set by the operator through the input device 3 and another case where the information calculated as the wall motion information is set as default.

Figure 5:
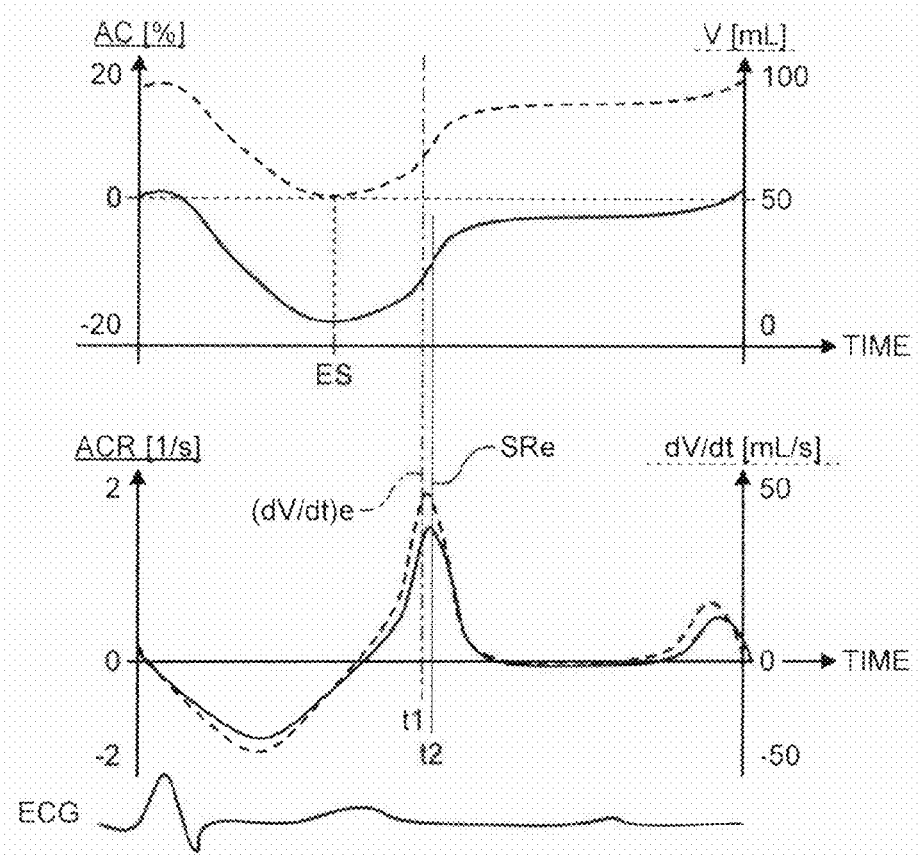
FIG. 5 and FIG. 6 are diagrams illustrating an extremum detection unit according to the first embodiment.
Figure 6:
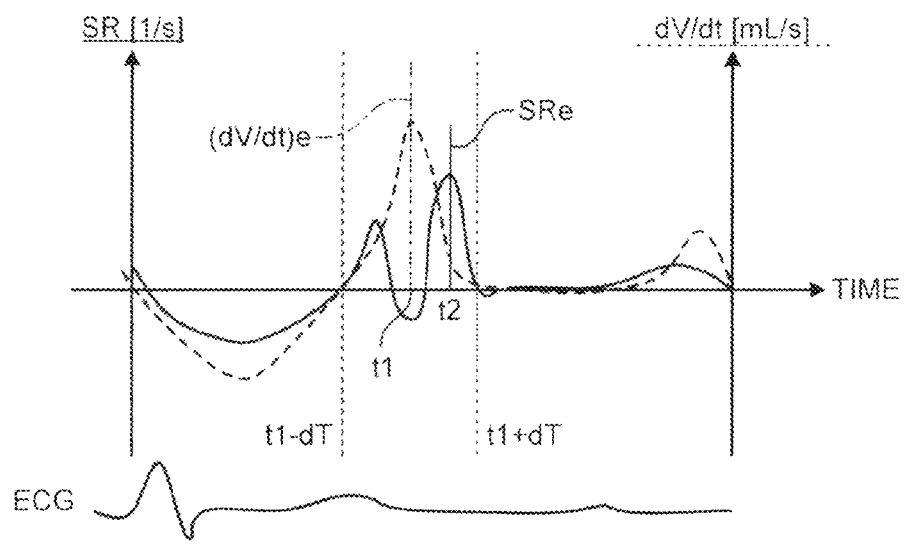

The time change rate calculator 17d illustrated in FIG. 2 calculates the first time-series data serving as time-series data of the time change rate of volume information from the time-series data of the volume information. The time change rate calculator 17d illustrated in FIG. 2 also calculates the second time-series data serving as time-series data of the time change rate of wall motion information from the time-series data of the wall motion information. The extremum detector 17e illustrated in FIG. 2 detects an extremum in early diastole of the first time-series data as the first extremum and detects an extremum in early diastole of the second time-series data as the second extremum. FIGS. 5 and 6 are diagrams illustrating an extremum detection unit according to the first embodiment.

In the upper diagram in FIG. 5, the dashed line illustrates a graph plotting time-series data of an inner cavity volume (V, unit: mL) calculated by the volume information calculator 17b and the solid line illustrates a graph plotting time-series data of the area change ratio (AC, unit: %) of the entire left ventricular endocardium calculated by the wall motion information calculator 17c. In the lower diagram in FIG. 5, the dashed line illustrates graph plotting time-series data of the time change rate (dV/dt, unit: mL/s) of the inner cavity volume calculated by the time change rate calculator 17d as the first time-series data and the solid line illustrates a graph plotting time-series data of the time change rate of the area change ratio (ACR, unit: 1/s) calculated by the time change rate calculator 17d as the second time-series data. A graph of ECG acquired from the electrocardiograph 4 is also illustrated.

In the case illustrated in FIG. 5, the extremum detector 17e detects a peak value "(dV/dt)e" of "dV/dt" as the first extremum in early diastole time phase. "e" here indicates "early diastole". In the case illustrated in FIG. 5, the extremum detector 17e also detects a peak value "SRe" of "ACR" as the second extremum in early diastole. "e" here indicates "early diastole" similarly to above. "SR" indicates "strain rate". AC is a form of the wall motion information as described above.

The extremum detector 17e first determines end systole (ES) in the time-series data to detect a peak value in early diastole. As the determination method of ES, a method is known in which the duration of aortic valve closure (AVC) of the subject P is measured in advance as an ejection period in measurement of the left ventricular outflow and the result from the measurement is referred to. A determination method of ES is also known in which the duration of the second sound is measured using phonocardiogram. In the first embodiment, these methods may be used, but they require separate measurement for determining ES.

The extremum detector 17e according to the first embodiment performs the estimation processing described below to easily determine ES without performing measurement. The extremum detector 17e estimates time phase in early diastole in the first time-series data using the time phase in which the volume information is minimum when detecting the first extremum.

For example, the extremum detector 17e detects time phase as "Es" in which "V" is minimum in a graph plotting time-series data in the inner cavity volume, as illustrated in the upper diagram in FIG. 5. The extremum detector 17e then explores candidates for the local maximum of "dV/dt" in an exploration period from the time phase detected as "ES" to an end diastole (ED). In this exploration period, two maximums that are an E-wave in early diastole accompanied by left ventricular enlargement and an A-wave in late diastole accompanied by atrial contraction emerge as the candidates.

The extremum detector 17e detects a local maximum close to the time phase detected as "ES" as "(dV/dt)e". In the case illustrated in the lower diagram in FIG. 5, the extremum detector 17e detects "dV/dt" at the time "t1" as "(dV/dt)e".

The extremum detector 17e then estimates time phase in early diastole in the second time-series data using the time phase in which the first extremum has been detected when detecting the second extremum. At this point, the time when "dV/dt" is the peak does not generally correspond to the time when "SR" is the peak. For this reason, the extremum detector 17e detects the peak value of the time change rate of the wall motion information in the time phase closest to the time phase in which the first extremum has been detected as the second extremum. In the case illustrated in the lower diagram in FIG. 5, the extremum detector 17e detects "ACR" at the time "t2" when ACR is the peak at the time closest to the time "t1" as "SRe".

When the wall motion information is "RS" or "displacement", the polarity in diastole is "negative", and when the wall motion information is information other than "RS" and "displacement", the polarity in diastole is "positive". The extremum detector 17e selects between negative and positive of the peak to be explored in accordance with the polarity of the peak value to be explored.

It is known that peculiar contraction called post systolic shortening (PSS) is generated by myocardial ischemia. When PSS occurs, there is a possibility that a plurality of peaks of "SR" emerge in early diastole. The extremum detector 17e may detect the maximum peak of "SR" in the range of the predetermined time period including the time phase in which the first extremum has been detected as "SRe". In an example illustrated in FIG. 6, the extremum detector 17e sets the time range ["t1−dT" to "t1+dT"] with respect to the time "t1" in which "(dV/dt)e" is detected. As illustrated in FIG. 6, the extremum detector 17e then detects "SR" at the time "t2" in which "SR" is maximum in the range ["t1−dT" to "t1+dT"] as "SRe".

Back to FIG. 2, the index calculator 17f calculates an index using the first extremum and the second extremum. For example, the index calculator 17f calculates "(dV/dt)e/SRe" that is the ratio between "(dV/dt)e" and "SRe" as an index. In other words, "(dV/dt)e" is used as "E" and "SRe" is used as "e'" in the first embodiment. In the first embodiment, "(dV/dt)e/SRe" is calculated as an index with respect to EDP instead of "E/e'". The index "(dV/dt)e/SRe" is displayed on the monitor 2 or output to an external device under the control of the control unit 18.

The volume information calculator 17b may calculate left ventricular ejection fraction (EF) from time-series data of volume information. EF is a value defined by left ventricular end-diastolic volume and left ventricular end-systolic volume. The volume information calculator 17b thus can acquire left ventricular end-diastolic volume and left ventricular end-systolic volume from time-series data of volume information, thereby calculating EF.

The volume information calculator 17b may also calculate the cardiac mass from time-series data of volume information. As described above, the volume information calculator 17b performs 3DT on the epicardial surface as well as the endocardial surface and generates time-series data for the period of one or more cardiac cycles of the volume surrounded by the epicardial surface. The volume information calculator 17b subtracts the inner cavity volume from the volume inside the epicardium in the same time phase, thereby calculating "cardiac volume (mL)". The volume information calculator 17b then multiplies the "cardiac volume (mL)" by a general cardiac density value (1.05 g/mL, for example), thereby calculating "cardiac mass (g)". The volume information calculator 17b may further normalize the "cardiac mass (g)" by "body surface area (BSA) (m$^2$)", thereby calculating "Mass-Index (g/m$^2$)".

The left ventricular ejection fraction, the cardiac volume, the cardiac mass, the Mass-Index, and the like calculated by the volume information calculator 17b are displayed together with the index on the monitor 2 or output to an external device under the control of the control unit 18.

Figure 7:
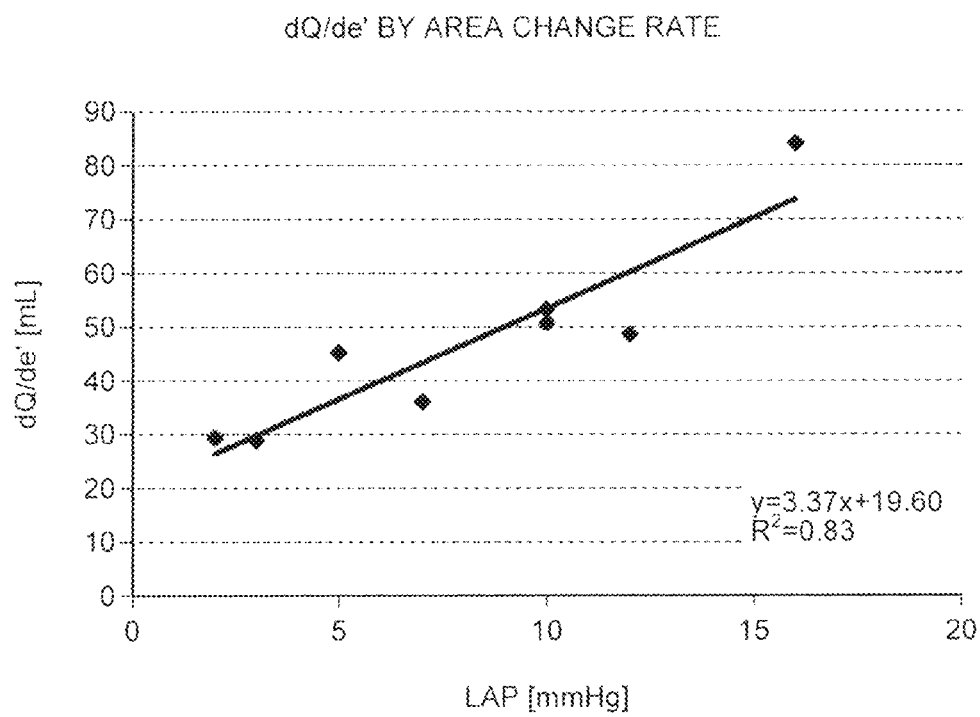
FIG. 7 is a diagram illustrating an example of an experiment employing image processing analysis according to the first embodiment.

FIG. 7 is a diagram illustrating an example of an experiment employing image processing analysis according to the first embodiment. FIG. 7 is an example of results from application of the analysis method described above to an experimental animal (dog). The vertical axis of the graph in FIG. 7 is "(dV/dt)e/SRe" calculated by the method described above when the peak value of temporal differential of AC (ACR) of the global endocardium is used as SRe. In FIG. 7, "(dV/dt)e/SRe" is indicated as "dQ/de'". The unit of "dQ/de'" is "[mL]=[mL/s]/[1/s]", showing the dimension of the volume. The horizontal axis of the graph in FIG. 7 indicates the left atrial pressure (LAP, unit: mmHg) measured using a cardiac catheter. LAP substantially equals to the left ventricular filling pressure. As exemplified in FIG. 7, the correlation function "$R^2$=0.83" demonstrates that an index calculated according to the present embodiment correlates well with LAP.

Figure 8:
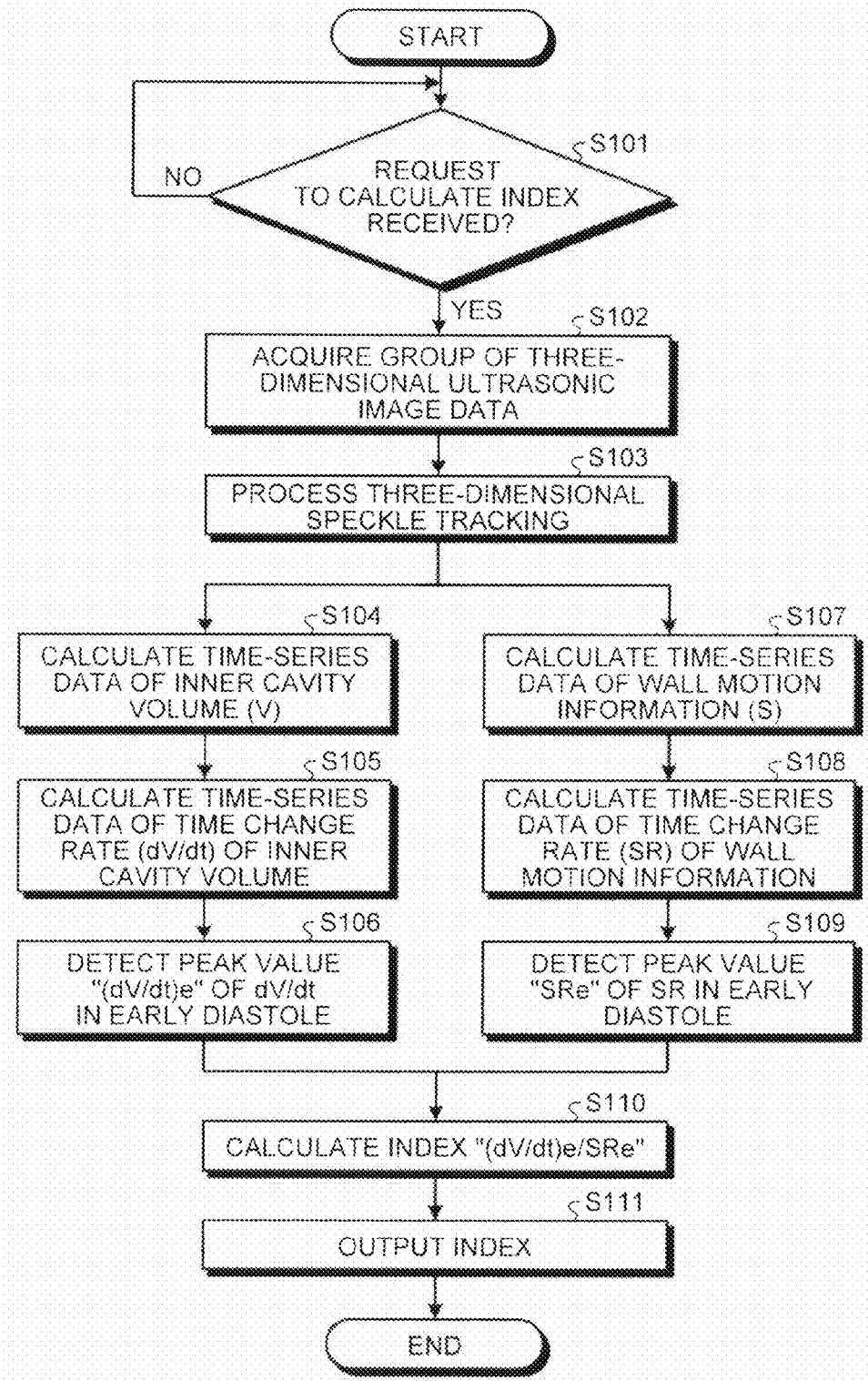
FIG. 8 is a flowchart illustrating an example of processing performed by the ultrasound diagnostic apparatus according to the first embodiment.

Described next is processing performed by the ultrasound diagnostic apparatus according to the first embodiment with reference to FIG. 8. FIG. 8 is a flowchart illustrating an example of processing performed by the ultrasound diagnostic apparatus according to the first embodiment.

As illustrated in FIG. 8, the ultrasound diagnostic apparatus according to the first embodiment determines if the group of three-dimensional ultrasonic image data to be processed has been specified and a request to calculate an index has been received (Step S101). When the request to calculate an index has not been received (No at Step S101), the ultrasound diagnostic apparatus waits until the request to calculate an index is received.

When the request to calculate an index has been received (Yes at Step S101), the image acquirer 17a acquires the group of three-dimensional ultrasonic image data thus specified (Step S102). The volume information calculator 17b performs three-dimensional speckle tracking processing with respect to the group of three-dimensional ultrasonic image data (Step S103).

The volume information calculator 17b calculates time-series data of the inner cavity volume (V) (Step S104) and the time change rate calculator 17d calculates time-series data of the time change rate (dV/dt) of the inner cavity volume (the first time-series data) through conversion using temporal differential of the time-series data of the inner cavity volume (V) (Step S105). The extremum detector 17e calculates the peak value "(dV/dt)e" in early diastole of dV/dt as the first extremum (Step S106). The extremum detector 17e estimates the time phase of early diastole in the first time-series data using the time phase in which the inner cavity volume is minimum.

In parallel with the processing in Step S104 to Step S106, the wall motion information calculator 17c calculates time-series data of the wall motion information (S) (Step S107) and the time change rate calculator 17d calculates time-series data (the second time-series data) of the time change rate (SR) of the wall motion information through conversion using temporal differential of the time-series data of the wall motion information (S) (Step S108). The extremum detector 17e calculates the peak value "SRe" in early diastole of SR as the second extremum (Step S109). The extremum detector 17e uses the time phase of the first extremum thus detected to perform processing of Step S109 after performing the processing of Step S106.

The index calculator 17f calculates the index "(dV/dt)e/SRe" (Step S110), outputs the index under the control of the control unit 18 (Step S111), and ends the processing.

As described above, according to the first embodiment, the speckle tracking technique, not the Doppler method, is used to acquire volume information and wall motion information in the same heart beat from the same three-dimensional moving image data (the group of three-dimensional ultrasonic image data). In the first embodiment, time-series data of the time change rate of volume information and time-series data of the time change rate of wall motion information in the same heart beat are acquired. If it is assumed that the area of the mitral annulus does not change in diastole, it is thought that the wave height "(dV/dt)e" in early diastole of "dV/dt" is proportional to the wave height of the E-wave at the left ventricular inflow velocity. In the first embodiment, therefore, the peak value "(dV/dt)e" of time-series data of the time change rate of volume information is detected as a value corresponding to "E" that conventionally used to be obtained using the Doppler method. Furthermore, in the first embodiment, the peak value "SRe" of time-series data of the time change rate of wall motion information is detected as a value corresponding to "e'" that conventionally used to be obtained using the Doppler method.

Actual patients with cardiac diseases have complications of cardiac dysrhythmia such as auricular fibrillation and extrasystole at high rates. Because cardiac dysrhythmia affects both "E" and "e'" values in measurement of "E/e'", synchronism of "E" and "e'" is required for accurate measurement of "E/e'".

In the first embodiment, "(dV/dt)e" and "SRe" are acquired from data of the same heart beat, "(dV/dt)e/SRe" is considered to be an index accurately reflecting EDP even when cardiac dysrhythmia occurs. In other words, the values of the denominator and the numerator in "(dV/dt)e/SRe" are values with which the synchronism is secured.

As described above, the Doppler method is not used in acquiring wall motion information in the first embodiment. Furthermore, information of the entire left ventricle is acquired all at once to acquire overall wall motion information (wall motion information of the entire left ventricle and wall motion information of the entire valve ring) in the first embodiment.

As described above, no error stemming from the dependency on Doppler angles will be generated in wall motion information when calculating an index in the first embodiment. The value corresponding to "e'" can be calculated from a plurality of local wall motion information in the first embodiment. Two values corresponding to "E" and "e'" can be calculated at the same heart beat in the first embodiment. Therefore, an index accurately reflecting left ventricular end-diastolic pressure can be calculated in the first embodiment.

Figure 9:
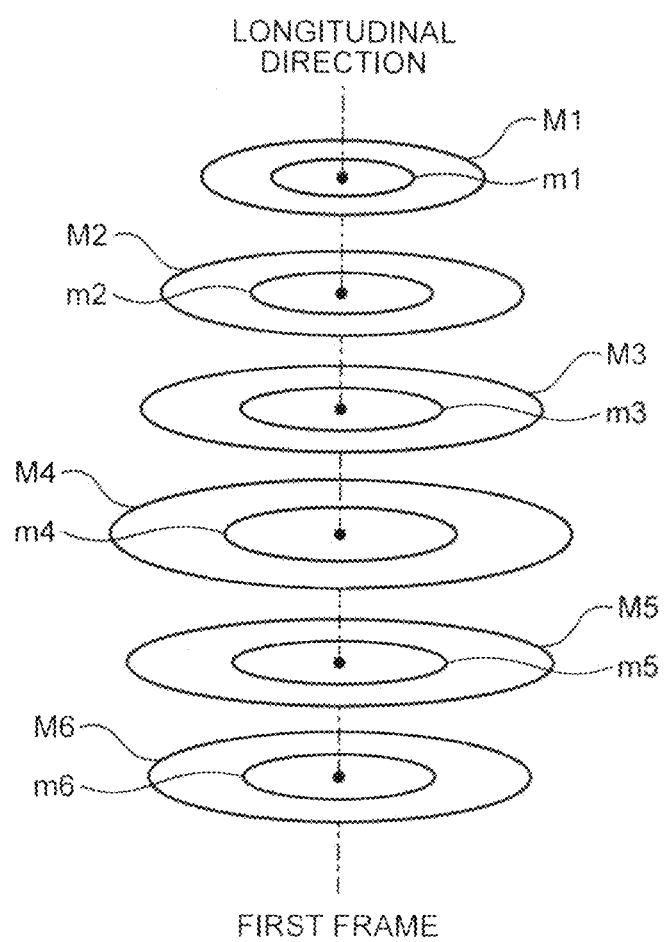
FIG. 9 is a diagram illustrating a first modification according to the first embodiment.
Figure 10:
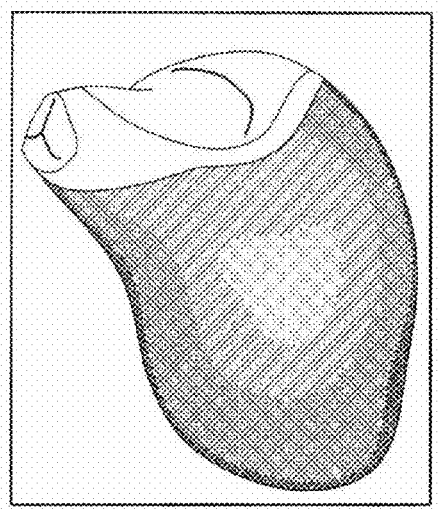
FIG. 10 is a diagram illustrating a second modification according to the first embodiment.

In the first embodiment, two modifications described below may be used for calculating the index described above. Modifications according to the first embodiment will be described below with reference to FIG. 9 and FIG. 10. FIG. 9 is a diagram illustrating a first modification according to the first embodiment. FIG. 10 is a diagram illustrating a second modification according to the first embodiment.

In the first modification, the volume information calculator 17b calculates time-series data of volume information using 2DT, not 3DT. For example, the volume information calculator 17b sets a plurality of sections perpendicular to the longitudinal direction with respect to three-dimensional ultrasonic image data (the first frame), as illustrated in FIG. 9. The volume information calculator 17b then sets a tracking point for each of closed curves (M1 to M6 . . . ) forming the epicardium and closed curves (m1 to m6 . . . ) forming the endocardium on each section as illustrated in FIG. 9. The volume information calculator 17b thus performs 2DT on a plurality of sections with respect to the group of three-dimensional ultrasonic image data.

The volume information calculator 17b then spatially interpolates and combines the results from the 2DT processing on the sections, thereby acquiring data corresponding to the results from the 3DT processing. The volume information calculator 17b uses the data thus acquired to calculate time-series data of the inner cavity volume (V). In the present modification, global, CS is preferably used as wall motion information. Furthermore, the wall motion information calculator 17c calculates time-series data of wall motion information by using the data generated by the volume information calculator 17b spatially interpolating and combining the results from 2DT processing. In this modification also, an index accurately reflecting left ventricular end-diastolic pressure can be calculated. As the direction of the sections in the present modification, a plurality of MPR longitudinal axis images may be used other than the MPR short axis images described above.

In the second modification, the volume information calculator 17b calculates time-series data of volume information with a method other than the speckle tracking technology. Specifically, the volume information calculator 17b performs calculation processing of volume information using the results from detecting the position of an inner cavity boundary as the first region of interest. More specifically, the volume information calculator 17b uses a known automatic contour detection technique such as edge detection related to image luminance distribution, and identifies the position of the left ventricular endocardium as illustrated in FIG. 10 (see the hatched region in FIG. 10). The volume information calculator 17b thus calculates time-series data of the inner cavity volume (V). The automatic contour detection processing may be performed by a processing unit other than the volume information calculator 17b.

In the second modification, the wall motion information calculator 17c performs calculation processing of wall motion information using the results from detecting the positions of the cardiac region as the second region of interest. The wall motion information calculator 17c calculates wall motion information using the results from the automatic contour detection performed by the volume information calculator 17b. In this case, the wall motion information calculator 17c preferably calculates the global area change ratio (AC) of the entire endocardial surface from the positional information of the left ventricular endocardial surface as wall motion information for detecting SRe. In the processing performed according to the present modification, the processing at Step S102 illustrated in FIG. 8 is substituted by the automatic contour detection processing. In this modification also, an index accurately reflecting left ventricular end-diastolic pressure can be calculated.

Second Embodiment

In a second embodiment, described is a case where the index described above is calculated using a group of two-dimensional ultrasonic image data.

The image processing unit 17 according to the second embodiment includes the same configuration as the image processing unit 17 according to the first embodiment illustrated in FIG. 2. In the second embodiment, however, a group of two-dimensional ultrasonic image data is to be processed by the image acquirer 17a, the volume information calculator 17b, and the wall motion information calculator 17c as described below.

The frame rate (volume rate) in a case where three-dimensional scanning is performed to collect a group of three-dimensional ultrasonic image data is around 20 to 30 frames per second, for example. In that case, the temporal resolution of the group of three-dimensional ultrasonic image data to be collected is lowered. This may cause variation in the time phase in which the first extremum or the second extremum is detected or underestimation of the first extremum or the second extremum. Widening the distance between the scan lines can improve the temporal resolution, but it will relatively lower the spatial resolution (bearing resolution) compared with the two-dimensional scanning.

For this reason, the operator first two-dimensionally scans a predetermined section of the left heart of the subject P for the period of one or more heart beats by apical approach, for example. The image generating unit 14 thus generates a plurality of pieces of two-dimensional ultrasonic image data along the time series for the period of one or more heart beats and stores the data thus generated in the image memory 15. The pieces of two-dimensional ultrasonic image data stored in the image memory 15 are a group of two-dimensional ultrasonic image data generated by ultrasonic scanning on the predetermined section of the heart including at least the left ventricle for the period of one or more heart beats. The two-dimensional ultrasonic image data according to the second embodiment is two-dimensional B-mode image data. In the second embodiment, both cases are acceptable: a case where the two-dimensional scanning is performed using an ultrasonic probe 1 that is a mechanical four-dimensional probe or a two-dimensional matrix array probe and another case where the two-dimensional scanning is performed using an ultrasonic probe 1 dedicated for two-dimensional scanning.

The image acquirer 17a according to the second embodiment acquires the group of two-dimensional ultrasonic image data generated by ultrasonic scanning on the predetermined section including at least the left ventricle for the period of one or more heart beat. The predetermined section described above is a section for imaging the longitudinal axis image. In the second embodiment, any one of apical four-chamber view (hereinafter, A4C), apical two-chamber view (hereinafter, A2C), or apical long-axis view (hereinafter, A3C) is used as two-dimensional ultrasonic image data of the longitudinal axis image.

Figure 11:
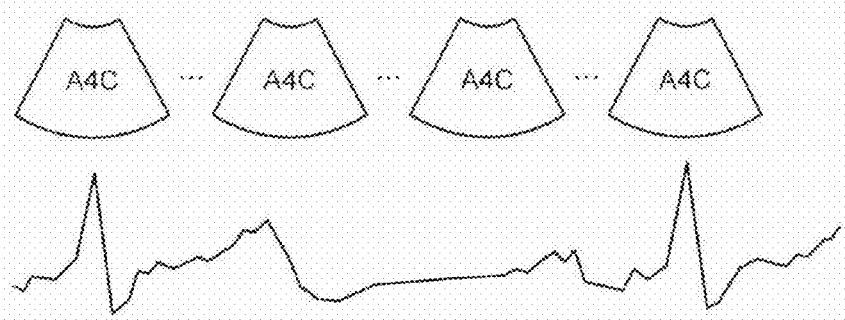
FIG. 11 is a diagram illustrating an image acquirer according to a second embodiment.

The image acquirer 17a according to the second embodiment acquires the group of two-dimensional ultrasonic image data generated by ultrasonic scanning on the predetermined section of the heart including at least the left ventricle (A4C plane, A3C plane, or A2C plane) for the period of one or more heart beats. FIG. 11 is a diagram illustrating an image acquirer according to the second embodiment. The image acquirer 17a acquires image data of a plurality of A4C planes along time series for the period of one or more heart beats, for example, as illustrated in FIG. 11.

Thereafter, the volume information calculator 17b according to the second embodiment calculates time-series data of volume information in the first region of interest in the left ventricle from the group of two-dimensional ultrasonic image data. The wall motion information calculator 17c according to the second embodiment calculates time-series data of wall motion information in the second region of interest in the left ventricle from the group of two-dimensional ultrasonic image data.

Specifically, the volume information calculator 17b according to the second embodiment performs calculation processing of volume information using the results from tracking the position of the first region of interest by means of processing including pattern matching between two-dimensional ultrasonic image data. The wall motion information calculator 17c according to the second embodiment performs calculation processing of wall motion information using the results from tracking the position of the second region of interest by means of processing including pattern matching between two-dimensional ultrasonic image data.

In other words, in the second embodiment, two-dimensional speckle tracking processing is performed. Described below is a case where 2DT processing is performed by the volume information calculator 17b. In the second embodiment, however, both cases are acceptable: a case where 2DT processing is performed by the image acquirer 17a and the wall motion information calculator 17c and another case where 2DT processing is performed by a processing unit other than the image processing unit 17 (the control unit 18, for example).

Figure 12:
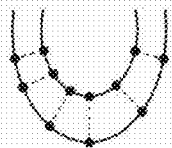
FIG. 12 is a diagram illustrating an example of two-dimensional speckle tracking.

FIG. 12 is a diagram illustrating an example of two-dimensional speckle tracking. For example, the input device 3 receives from an operator a request to display the group of two-dimensional ultrasonic image data in the first frame. The control unit 18 to which the request to display is transferred reads out the two-dimensional ultrasonic image data in the first frame and causes the monitor 2 to display the data thus read out.

Thereafter, the operator refers to the two-dimensional ultrasonic image data displayed on the monitor 2 to set a plurality of tracking points for 2DT. To cite an example, the operator traces the points of the left ventricular endocardium and the epicardium in the two-dimensional ultrasonic image data. The volume information calculator 17b reconstructs two-dimensional boundary surfaces from the endocardium and the epicardium thus traced. The volume information calculator 17b then sets a plurality of tracking points paired on each of the endocardium and epicardium in the first frame as illustrated in FIG. 12. The volume information calculator 17b sets template data to each of the tracking points set in the first frame. The template data consist of a plurality of pixels centering on a tracking points.

The volume information calculator 17b then explores a region that fits to the speckle pattern of the template data between the two frames the most, thereby tracking to which position the template data is moved in the next frame. The tracking point may be set by the volume information calculator 17b detecting the endocardium and the epicardium of the left ventricle included in the first frame.

Figure 13:
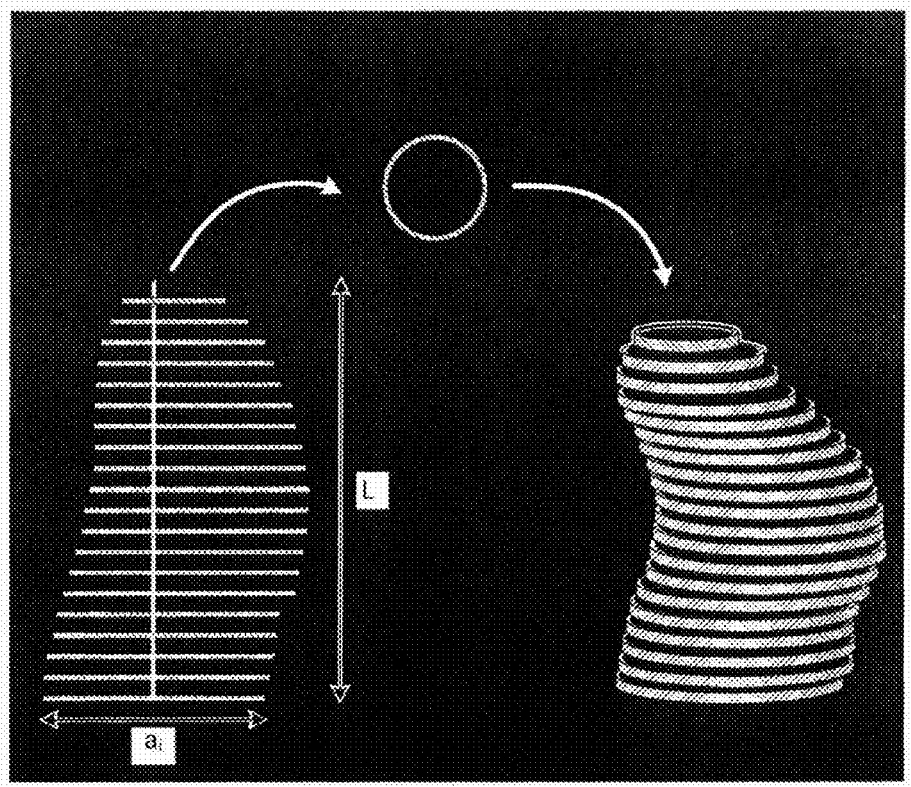
FIG. 13 is a diagram illustrating a volume information calculator according to the second embodiment.

The volume information calculator 17b then approximately calculates the inner cavity volume (V) using the "area-length method" and the "Simpson method" estimating the three-dimensional inner cavity shape from the contour of the two-dimensional image. FIG. 13 is a diagram illustrating a volume information calculator according to the second embodiment.

The volume information calculator 17b calculates time-series data approximating the inner cavity volume by performing the Simpson method as illustrated in FIG. 13, for example. When performing the Simpson method, the volume information calculator 17b divides the A4C image equally into twenty discs perpendicular to the longitudinal axis (L) as illustrated in FIG. 13. The volume information calculator 17b then calculates the distance between two points where the i-th disc intersects with the endocardial surface (see $a_i$ in FIG. 13). The volume information calculator 17b then approximates the three-dimensional shape of the inner cavity in the i-th disc as a slice of a column of the diameter "$a_i$," as illustrated in FIG. 13. The volume information calculator 17b calculates the sum of the volume of the twenty columns as volume information approximating the inner cavity volume. The volume information calculator 17b thus calculates time-series data of the volume information.

The "area-length method" presumes the left ventricle as a spheroid and calculates the length of the short axis of the left ventricular inner cavity from the results of measurement of the left ventricular inner cavity area including the left ventricular longitudinal axis and the left ventricular inner cavity longitudinal axis length, thereby calculating an approximate value of the inner cavity. The volume information calculator 17b calculates the left ventricular inner cavity short axis length by measuring the left ventricular inner cavity area and the left ventricular inner cavity longitudinal axis length from the results of 2DT processing, thereby calculating the volume information approximating the inner cavity volume.

The wall motion information calculator 17c according to the second embodiment uses a two-dimensional longitudinal axis image, and therefore calculates any of strain in the longitudinal direction (LS), displacement in the longitudinal axis (LD), a moving distance (AD), displacement in the wall thickness direction (RD), or "transverse strain (TS)", that is, the wall thickness change rate in the longitudinal axis image as the types of wall motion information. From the viewpoint of a value corresponding to the mitral annulus tissue velocity, LS or LD in parallel with the longitudinal direction is preferably used.

Furthermore, the wall motion information calculator 17c according to the second embodiment uses a two-dimensional longitudinal axis image, and therefore preferably calculates an overall average of the endocardium in LS, TS, and RD and calculates an average in two-divided regions of the right side and the left side of the mitral annulus in LD and AD as definition regions of wall motion information.

In the second embodiment, the calculation processing performed by the time change rate calculator 17d, the detection processing performed by the extremum detector 17e, the calculation processing performed by the index calculator 17f are the same as those in the first embodiment. The index is displayed on the monitor 2 or output to an external device under the control of the control unit 18.

The volume information calculator 17b according to the second embodiment may further calculate the left ventricle ejection fraction from the time-series data of the inner cavity volume calculated by the approximation. The volume information calculator 17b according to the second embodiment may also calculate an approximate value of the volume inside the epicardium from the results of 2DT, thereby calculating the cardiac volume, the cardiac mass, and the Mass-Index. The left ventricle ejection fraction, the cardiac volume, the cardiac mass, the Mass-Index, and the like that the volume information calculator 17b calculates are displayed on the monitor 2 or output to an external device under the control of the control unit 18.

Described next with reference to FIG. 14 will be processing performed by an ultrasound diagnostic apparatus according to the second embodiment. FIG. 14 is a flowchart illustrating an example of processing performed by an ultrasound diagnostic apparatus according to the second embodiment.

As illustrated in FIG. 14, the ultrasound diagnostic apparatus according to the second embodiment determines if a group of two-dimensional ultrasonic image data to be processed has been specified and a request to calculate an index has been received (Step S201). When the request to calculate has not been received (No at Step S201), the ultrasound diagnostic apparatus waits until the request to calculate is received.

When the request to calculate an index has been received (Yes at Step S201), the image acquirer 17a acquires the group of two-dimensional ultrasonic image data thus specified (Step S202). The volume information calculator 17b performs two-dimensional speckle tracking processing with respect to the group of two-dimensional ultrasonic image data (Step S203).

The volume information calculator 17b approximately calculates time-series data of the inner cavity volume (V) (Step S204) and the time change rate calculator 17d calculates time-series data of the time change rate (dV/dt) of the inner cavity volume (the first time-series data) through conversion using temporal differential of the time-series data of the inner cavity volume (V) (Step S205). The extremum detector 17e calculates the peak value "(dV/dt)e" in early diastole of dV/dt as the first extremum (Step S206). The extremum detector 17e estimates the time phase of early diastole in the first time-series data using the time phase in which the inner cavity volume is minimum at step S206.

In parallel with the processing in Step S204 to Step S206, the wall motion information calculator 17c calculates time-series data of the wall motion information (S) (Step S207) and the time change rate calculator 17d calculates time-series data (the second time-series data) of the time change rate (SR) of the wall motion information through conversion using temporal differential of the time-series data of the wall motion information (S) (Step S208). The extremum detector 17e calculates the peak value "SRe" in early diastole of SR as the second extremum (Step S209). The extremum detector 17e uses the time phase of the first extremum thus detected to perform processing of Step S209 after performing the processing of Step S206.

The index calculator 17f calculates the index "(dV/dt)e/SRe" (Step S210), outputs the index under the control of the control unit 18 (Step S211), and ends the processing.

As described above, in the second embodiment, restrictions on both the temporal resolution and the spatial resolution are improved by using two-dimensional moving image data compared with the first embodiment using three-dimensional moving image data. Two-dimensional scanning can provide moving image data of around 60 to 80 frames per second (fps) even if the scanning intervals are set sufficiently small to raise the bearing resolution compared with three-dimensional scanning. Accordingly, in the second embodiment, variation in the time phase in which the first extremum or the second extremum is detected and underestimation of the first extremum or the second extremum can be prevented.

However, in the second embodiment, because wall motion information is estimated using information on one section, there is a restriction compared to the first embodiment that a value corresponding to "e'" can be acquired only from a region that is spatially restricted. Furthermore, there are cases where a value corresponding to "E" includes an error stemming from the underlying bulking value that is estimated from a two-dimensional section.

The method described in the second embodiment using the two-dimensional moving image having high temporal resolution is preferably applied when it is important to secure the synchronism of the denominator and the numerator with which the index is calculated. Specifically, in cases where the period of heart beats are not constant such as atrial fibrillation, the synchronism of values corresponding to "E" and "e'" is important. Therefore, the method described in the second embodiment can function effectively.

In the second embodiment, an automatic contour detection technique may also be applied instead of 2DT similarly to the second modification according to the first embodiment. In that case, the wall motion information calculator 17c preferably calculates the change rate of the overall length of the entire endocardium as "LS" serving as wall motion information used for calculating an index from the positional information of the left ventricular endocardial contour. In the processing performed in the present modification, the processing at Step S202 illustrated in FIG. 14 is substituted by the automatic contour detection processing.

The present modification can also provide an index correlating with EDP even when using the information of a part of the inner cavity area surrounded by the contour as the numerator of the index instead of the inner cavity volume. In that case, when presuming that the wall motion information is the strain rate (unit: 1/s), the unit of the index eventually obtained has the dimension of the area, that is "$cm^2$".

Third Embodiment

In a third embodiment, described is cases where the index described above is calculated using a plurality of groups of two-dimensional ultrasonic image data.

The image processing unit 17 according to the third embodiment includes the same configuration as the image processing unit 17 according to the first embodiment illustrated in FIG. 2. However, in the third embodiment, a plurality of groups of two-dimensional ultrasonic image data is to be processed by the image acquirer 17a, the volume information calculator 17b, and the wall motion information calculator 17c as described below.

In the third embodiment, the operator first two-dimensionally scans each of the sections as predetermined sections of the left heart of the subject P for the period of one or more heart beats by apical approach. For example, the operator two-dimensionally scans each of the two or more sections selected from the sections for the apical four-chamber view (A4C), the apical two-chamber view (A2C), and the apical long-axis view (A3C) for the period of one or more heart beats sequentially. The image generating unit 14 thus generates a plurality of pieces of two-dimensional ultrasonic image data along time series for the period of one or more heart beats for each of the sections and stores the data thus generated in the image memory 15. The two-dimensional ultrasonic image data for each of the sections stored in the image memory 15 is the groups of two-dimensional ultrasonic image data generated by ultrasonic scanning on each of the sections of the heart including at least the left ventricle for the period of one or more heart beats. The two-dimensional ultrasonic image data according to the third embodiment is collected using an ultrasonic probe 1 dedicated for two-dimensional scanning.

The image acquirer 17a according to the third embodiment acquires the groups of two-dimensional ultrasonic image data generated by ultrasonic scanning on each of the sections of the heart including at least the left ventricle for the period of one or more heart beats. The image acquirer 17a acquires a plurality of groups of two-dimensional ultrasonic image data corresponding to each of a plurality of sections as predetermined sections.

Figure 15A:
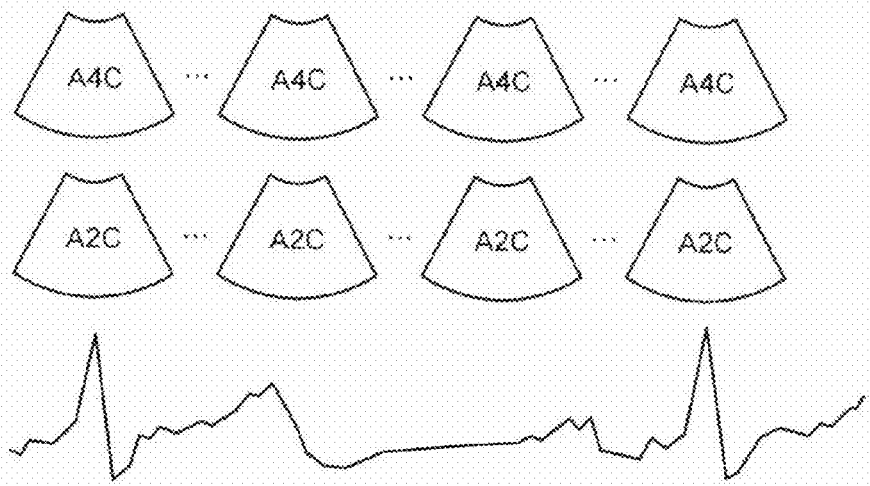
FIG. 15A and FIG. 15B are diagrams illustrating an image acquirer according to a third embodiment.
Figure 15B:
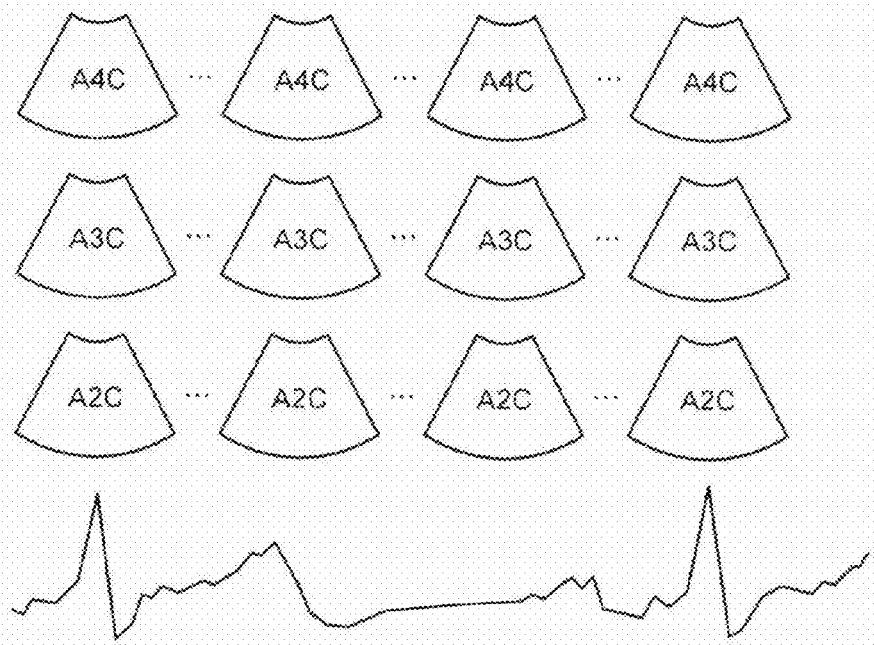

FIGS. 15A and 15B each are a diagram illustrating an image acquirer according to the third embodiment. As illustrated in FIG. 15A, the image acquirer 17a acquires a plurality of pieces of image data of A4C along time series of one or more heart beats and a plurality of pieces of image data of A2C along time series of one or more heart beats, for example.

Alternatively, the image acquirer 17a acquires a plurality of pieces of image data of A4C along time series of one or more heart beats, a plurality of pieces of image data of A3C along time series of one or more heart beats, and a plurality of pieces of image data of A2C along time series of one or more heart beats, as illustrated in FIG. 15B.

The volume information calculator 17b according to the third embodiment calculates time-series data of volume information in the first region of interest in the left ventricle from a plurality of groups of two-dimensional ultrasonic image data. The wall motion information calculator 17c according to the third embodiment calculates time-series data of wall motion information in the second region of interest in the left ventricle from the groups of two-dimensional ultrasonic image data.

Specifically, the volume information calculator 17b according to the third embodiment performs calculation processing of volume information using the results of tracking the position of the first region of interest by means of processing including pattern matching between two-dimensional ultrasonic image data similarly to the second embodiment. The wall motion information calculator 17c according to the third embodiment performs calculation processing of wall motion information using the results of tracking the second region of interest by means of processing including pattern matching between two-dimensional ultrasonic image data, similarly to the second embodiment.

In other words, in the third embodiment, two-dimensional speckle tracking processing is performed in each of a plurality of groups of two-dimensional ultrasonic image data. Described below is a case where 2DT processing is performed by the volume information calculator 17b. However, in the third embodiment, both cases are acceptable: a case where 2DT processing is performed by the image acquirer 17a or the wall motion information calculator 17c and another case where 2DT processing is performed by a processing unit (the control unit 18, for example) other than the image processing unit 17.

In the third embodiment, when using an ultrasonic probe 1 dedicated for two-dimensional scanning, the groups of two-dimensional ultrasonic image data for each section are collected in different times individually. The volume information calculator 17*b* arrays each group of two-dimensional ultrasonic image data with R-waves and P-waves as the reference time phases and with two-dimensional ultrasonic image data of the R-waves and P-waves at the head, for example. The volume information calculator 17*b* thus substantially matches the time phases between the group of the ultrasonic image data of A4C and the group of the ultrasonic image data of A2C along the time series, for example. The volume information calculator 17*b* may select the groups of two-dimensional ultrasonic image data in which the R-wave intervals and the P-wave intervals or the ECG forms substantially correspond to each other from each of the groups of two-dimensional ultrasonic image data to substantially match the time phases of each group of two-dimensional ultrasonic image data. Both cases are acceptable: a case where the processing for matching the time phases is performed by the image acquirer 17*a* or the wall motion information calculator 17*c* and another case where the processing for matching the time phases is performed by a processing unit other than the image processing unit 17 (the control unit 18, for example). In the third embodiment, however, an ultrasonic probe 1 that is a two-dimensional matrix array probe may be used to simultaneously perform two-dimensional scanning for a plurality of sections. In that case, processing for matching the time phases is not necessarily performed in the third embodiment.

Figure 16A:
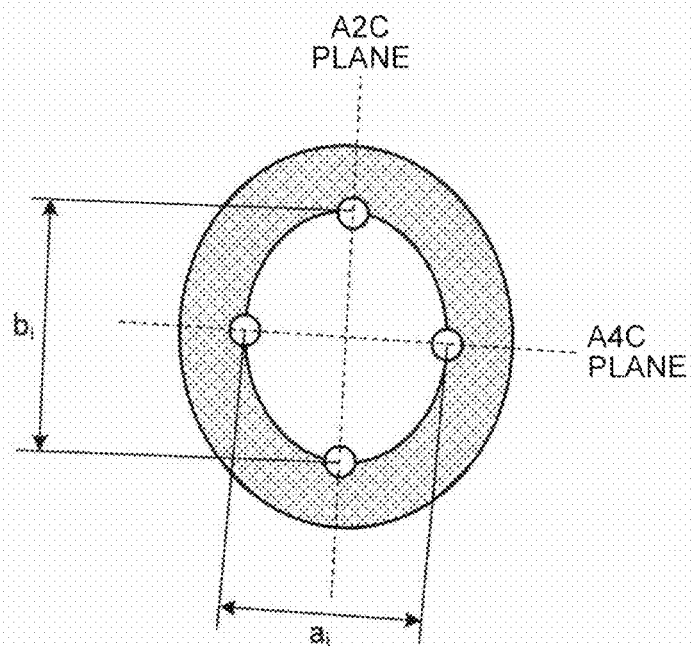
FIG. 16A and FIG. 16B are diagrams illustrating a volume information calculator according to the third embodiment.
Figure 16B:
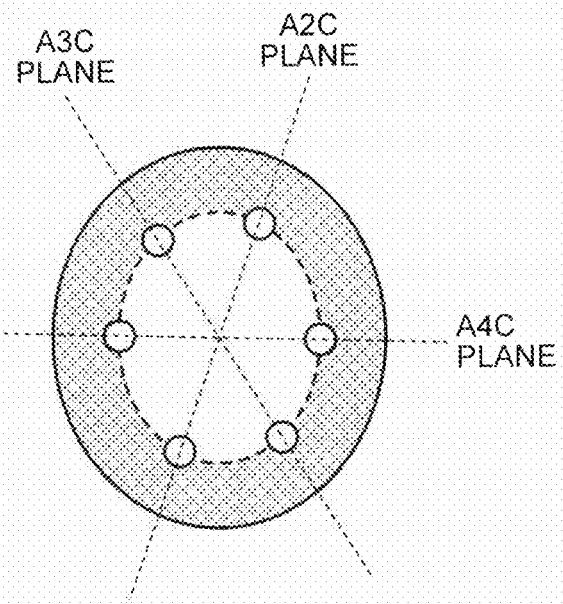

The volume information calculator 17*b* according to the third embodiment acquires the position of the tracking point corresponding to the endocardium in each piece of two-dimensional ultrasonic image data (specifically, the position of the inner cavity contour) from the results of 2DT processing of two-dimensional ultrasonic image data for each of the sections in the same time phase. The volume information calculator 17*b* then approximately calculates the inner cavity volume (V) from the position of the inner cavity contour using the "modified-Simpson method" that is a modification method of the "Simpson method" estimating the three-dimensional shape of the inner cavity. FIGS. 16A and 16B each are a diagram illustrating a volume information calculator according to the third embodiment.

When two-dimensional scanning is performed for each of the two sections of the A4C plane and the A2C plane, the volume information calculator 17*b* divides each of the A4C image and the A2C image in the same time phase equally into twenty discs perpendicular to the longitudinal axis, for example. The volume information calculator 17*b* then calculates the distance between two points where the i-th disc of the A4C image intersects with the endocardial surface (see $a_i$ in FIG. 16A) and the distance between two points where the i-th disc of the A2C image intersects with the endocardial surface (see $b_i$ in FIG. 16A), as illustrated in FIG. 16A. The volume information calculator 17*b* then approximates the three-dimensional shape of the inner cavity of the i-th disc as a slice of an ellipsoid having a major axis and a minor axis estimated from "$a_i$" and "$b_i$". The volume information calculator 17*b* calculates the sum of the volume of the twenty ellipsoids as volume information obtained by approximation of the inner cavity volume. The volume information calculator 17*b* thus calculates time-series data of the volume information.

When two-dimensional scanning on each of the A4C plane, the A3C plane, and the A2C plane is performed, the volume information calculator 17*b* divides each of the A4C image, the A3C image, and the A2C image equally into twenty discs perpendicular to the longitudinal axis, for example. The volume information calculator 17*b* then acquires the positions of two points where the i-th disc of the A4C image intersects with the endocardial surface, the positions of two points where the i-th disc of the A3C image intersects with the endocardial surface, and the positions of two points where the i-th disc of the A2C image intersects with the endocardial surface. The volume information calculator 17*b* then determines the inner cavity shape of the i-th disc from the positions of the six points thus acquired using the "spline interpolation" (see the dotted closed curve illustrated in FIG. 16B), for example. The volume information calculator 17*b* then approximates the three-dimensional shape of the inner cavity in the i-th disc as a cylinder slice with the spline closed curves serving as the top plane and the bottom plane. The volume information calculator 17*b* calculates the sum of the volumes of the twenty discs as volume information obtained by approximation of the inner cavity volume. The volume information calculator 17*b* thus calculates time-series data of the volume information. The time change rate calculator 17*d* performs temporal differential of the time-series data of volume information, thereby calculating the first time-series data, and the extremum detector 17*e* detects the first extremum "(dV/dt)e" from the first time-series data. The extremum detector 17*e* estimates the time phase of ES for detecting the first extremum using the method described in the first embodiment.

The wall motion information calculator 17*c* according to the third embodiment generates time-series data of wall motion information on each section. The types of various wall motion information and the definition regions of wall motion information in the third embodiment are basically the same as in the second embodiment.

When wall motion information defined on one section is set as wall motion information in the second region of interest, the wall motion information calculator 17*c* according to the third embodiment generates time-series data of the wall motion information on the section concerned. For example, the wall motion information calculator 17*c* generates time-series data of wall motion information of the A4C plane (average of wall motion information on two points, for example). In that case, the time change rate calculator 17*d* performs temporal differential of time-series data of one piece of wall motion information output from the wall motion information calculator 17*c*, thereby calculating the second time-series data, and the extremum detector 17*e* detects the second extremum "SRe" from the second time-series data. The extremum detector 17*e* detects the second extremum using the time phase in which the first extremum has been detected. The index calculator 17*f* calculates an index by dividing the first extremum by the second extremum.

When wall motion information defined by each of the sections is set as wall motion information in the second region of interest, the output form of the data output to the time change rate calculator 17*d* from the wall motion information calculator 17*c* is roughly classified into the two output forms described below, in the third embodiment.

When the first output form is performed, the wall motion information calculator 17*c* calculates time-series data obtained by averaging the time-series data of the wall motion information of each of the groups of two-dimensional ultrasonic image data as time-series data of wall motion information. For example, in the first output form, the wall motion information calculator 17*c* calculates time-series data of LS of the A4C (time-series data of the average of LS at two positions on the A4C plane, for example) and time-series data of LS of the A2C (time-series data of the average of LS at two positions on the A2C plane, for example). The wall motion information calculator 17c calculates time-series data of the average (S') of the time-series data of LS of the A4C plane and the time-series data of LS of the A2C plane.

The time change rate calculator 17d that has received the time-series data of the averaged wall motion information from the wall motion information calculator 17c performs temporal differential of "time-series data of S'", thereby calculating the second time-series data (time-series data of SR'), and the extremum detector 17e detects the second extremum "SR'e" from the second time-series data (time-series data of SR'). The extremum detector 17e detects the second extremum using the time phase in which the first extremum has been detected. The index calculator 17f calculates an index value by dividing the first extremum by the second extremum.

When the second output form is performed, the wall motion information calculator 17c calculates a plurality of pieces of time-series data of wall motion information corresponding to the groups of two-dimensional ultrasonic image data. The time change rate calculator 17d calculates a plurality of pieces of the second time-series data from the respective pieces of the time-series data of wall motion information. The extremum detector 17e calculates the value obtained by averaging the extremum in early diastole detected in each of the pieces of the second time-series data as the second extremum. For example, in the second output form, the wall motion information calculator 17c calculates time-series data of LS of the A4C plane and time-series data of LS of the A2C plane. The time change rate calculator 17d calculates the second time-series data of the A4C plane and the second time-series data of the A2C plane as the second time-series data, for example.

The extremum detector 17e detects an extremum in early diastole of the second time-series data of the A4C plane and an extremum in early diastole of the second time-series data of the A2C plane, for example. The extremum detector 17e uses the time phase in which the first extremum has been detected to detect an extremum of each of the second time-series data of the A4C plane and the second time-series data of the A2C plane, for example. The extremum detector 17e then averages the extremum of the second time-series data of the A4C plane and the extremum of the second time-series data of the A2C plane, thereby calculating the second extremum "SR'e". The index calculator 17f calculates an index by dividing the first extremum by the second extremum.

The first output form is considered to be suitable for obtaining an averaged peak value with the effect of the region of extremely poor motion being lessened, for cases where the motion of the heart is extremely poor locally, such as myocardial infarction. In contrast, the second output form is considered to be suitable for obtaining a global peak value including the variations among the regions, for cases of dyssynchrony such as left bundle branch block where the index values of regional wall motion (e.g. strain) and its peak timing vary.

The index calculated by the index calculator 17f is displayed on the monitor 2 or output to an external device under the control of the control unit 18.

The volume information calculator 17b according to the third embodiment may further calculate the left ventricular ejection fraction from the time-series data of the inner cavity volume approximately calculated. Furthermore, the volume information calculator 17b according to the third embodiment may calculate an approximate value of the internal volume of the epicardium from the results of 2DT processing, thereby calculating an approximate value of the cardiac volume, the cardiac mass, and the Mass-Index. The approximate values of the left ventricular ejection fraction, the cardiac volume, the cardiac mass, and the Mass-Index, calculated by the volume information calculator 17b, for example, are displayed on the monitor 2 or output to an external device together with the index value under the control of the control unit 18.

Figure 17:
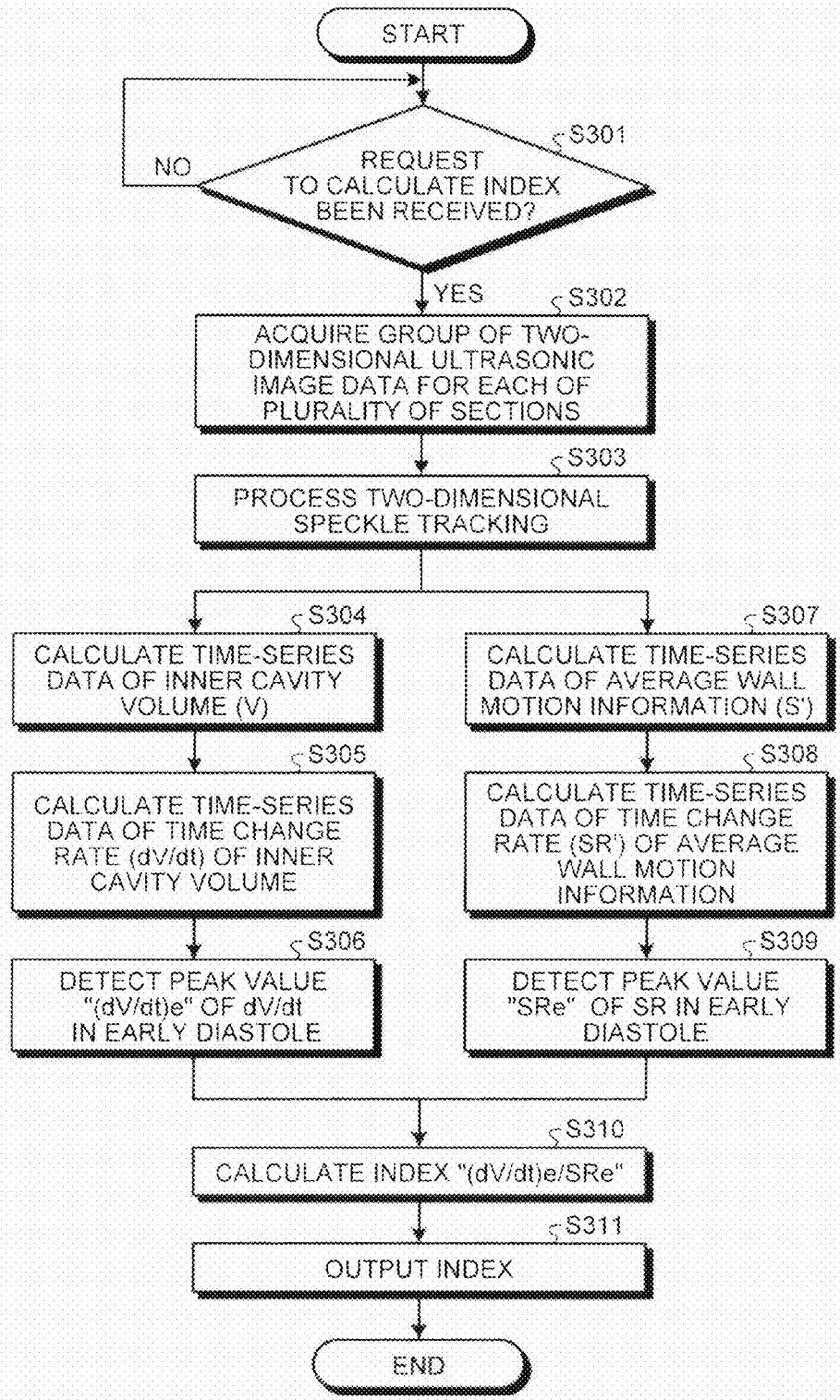
FIG. 17 is a flowchart illustrating an example of processing performed by an ultrasound diagnostic apparatus according to the third embodiment.

Described next is processing performed by an ultrasound diagnostic apparatus according to the third embodiment with reference to FIG. 17. FIG. 17 is a flowchart illustrating an example of processing performed by an ultrasound diagnostic apparatus according to the third embodiment. The flowchart illustrated in FIG. 17 represents an example of processing in which the first output form is performed.

As illustrated in FIG. 17, the ultrasound diagnostic apparatus according to the third embodiment determines if the group of two-dimensional ultrasonic image data for each of the sections to be processed has been specified and a request to calculate an index has been received (Step S301). When the request to calculate an index has not been received (No at Step S301), the ultrasound diagnostic apparatus waits until the request to calculate an index is received.

When the request to calculate an index has been received (Yes at Step S301), the image acquirer 17a acquires the group of two-dimensional ultrasonic image data for each of the sections thus specified (Step S302). The volume information calculator 17b performs two-dimensional speckle tracking processing with respect to each of the groups of two-dimensional ultrasonic image data (Step S303).

The volume information calculator 17b approximately calculates time-series data of the inner cavity volume (V) (Step S304) and the time change rate calculator 17d calculates time-series data of the time change rate (dV/dt) of the inner cavity volume (the first time-series data) through conversion using temporal differential of the time-series data of the inner cavity volume (V) (Step S305). The extremum detector 17e calculates the peak value "(dV/dt)e" in early diastole of dV/dt as the first extremum (Step S306). The extremum detector 17e estimates the time phase of early diastole in the first time-series data using the time phase in which the inner cavity volume is minimum at Step S306.

In parallel with the processing in Step S304 to Step S306, the wall motion information calculator 17c calculates time-series data of the wall motion information of each of the sections and averages a plurality of pieces of the time-series data of the wall motion information, thereby calculating time-series data of averaged wall motion information (S') (Step S307). The time change rate calculator 17d calculates time-series data (the second time-series data) of the time change rate (SR') of the averaged wall motion information through conversion using temporal differential of the time-series data of the averaged wall motion information (Step S308). The extremum detector 17e calculates the peak value "SRe" in early diastole of SR as the second extremum (Step S309). The extremum detector 17e uses the time phase of the first extremum thus detected to perform processing of Step S309 after performing the processing of Step S306.

The index calculator 17f calculates the index "(dV/dt)e/SRe" (Step S310), outputs the index under the control of the control unit 18 (Step S311), and ends the processing.

As described above, in the third embodiment, a plurality of pieces of two-dimensional moving image data are used in which the temporal resolution and the spatial resolution are secured, thereby obtaining a more "overall value" for the value corresponding to "e'" compared with the second embodiment. This reduces the possibility that the value corresponding to "e'" includes an error. In the third embodiment, the approximation accuracy of the inner cavity volume can also be improved using a plurality of pieces of two-dimensional moving image data compared with the second embodiment.

The method described in the third embodiment is suitably applied to cases where the totality of the value corresponding to "e'" is more important than the synchronism of the values corresponding to "E" and "e'". For example, in cases where the period of heart beats is constant, the synchronism of the values corresponding to "E" and "e'" is secured to some extent. Therefore, the method described in the third embodiment can effectively function in cases such as myocardial infarction where the period of heart beats is constant but estimating V from only one section will decrease accuracy due to an unusual shape present locally.

In the third embodiment also, an automatic contour detection technique may be applied instead of 2DT processing similarly to the second modification according to the first embodiment. In the processing performed by the present modification, Step S302 illustrated in FIG. 17 is substituted by automatic contour detection processing.

In the third embodiment, cases are acceptable where 2DT is performed using a plurality of short axis images, not a plurality of longitudinal axis images, to interpolate and combine the position of the contour of the inner cavity, thereby acquiring volume information at the same time acquiring wall motion information defined from the short axis image (CS or RS, suitably) from a plurality of sections. In this modification, to improve the volume estimation precision, short axis images of approximately three to seven sections with different levels with respect to the longitudinal axis are preferably combined.

Described above in the first to the third embodiments are cases where processing on groups of ultrasonic image data is performed in an ultrasound diagnostic apparatus. However, the image processing method described above in the first to the third embodiments may be performed by an image processing apparatus installed separately from the ultrasound diagnostic apparatus. In that case, the image processing apparatus performs an image processing method described above by receiving groups of ultrasonic image data received from an ultrasound diagnostic apparatus, a database of PACS, or a database of an electronic health record system.

The image processing method described above in the first to the third embodiments can be performed by executing an image processing program prepared in advance on a computer such as a personal computer and a workstation. This image processing program can be distributed through a network such as the Internet. The image processing program can also be recorded in a non-temporary storage medium that can be read by a computer, such as a hard disc, a flexible disk (FD), a CD-ROM, an MO, a DVD, and a flash memory such as a USB memory and an SD card memory and read out from such a non-temporary storage medium by a computer.

As described above, according to the first to the third embodiments, an index accurately reflecting left ventricular end-diastolic pressure can be calculated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus, comprising:
a processor configured to:
acquire a group of ultrasonic image data generated by ultrasonic scanning on a heart including at least a left ventricle for a period of one or more heart beats;
calculate, from the group of the ultrasonic image data, time-series data of volume in a first region of interest in the left ventricle;
calculate, from the group of the ultrasonic image data, time-series data of wall motion in a second region of interest in the left ventricle;
calculate, from the time-series data of the volume, first time-series data that is time-series data of a time change rate of the volume; and
calculate, from the time-series data of the wall motion, second time-series data that is time-series data of a time change rate of the wall motion;
detect an extremum in early diastole of the first time-series data as a first extremum;
detect an extremum in early diastole of the second time-series data as a second extremum; and
calculate an index using the first extremum and the second extremum.

2. The ultrasound diagnostic apparatus according to claim 1, wherein the processor is further configured to:
acquire a group of three-dimensional ultrasonic image data generated by ultrasonic scanning on a heart including at least the left ventricle for the period of one or more heart beats,
calculate the time-series data of the volume from the group of three-dimensional ultrasonic image data, and
calculate the time-series data of the wall motion from the group of three-dimensional ultrasonic image data.

3. The ultrasound diagnostic apparatus according to claim 1, wherein the processor is further configured to:
acquire a group of two-dimensional ultrasonic image data generated by ultrasonic scanning on a predetermined section of a heart including at least the left ventricle for the period of one or more heart beats,
calculate, from the group of the two-dimensional ultrasonic image data, the time-series data of the volume in the first region of interest in the left ventricle, and
calculate, from the group of the two-dimensional ultrasonic image data, the time-series data of the wall motion in the second region of interest in the left ventricle.

4. The ultrasound diagnostic apparatus according to claim 3, wherein the processor is further configured to:
acquire a plurality of groups of two-dimensional ultrasonic image data corresponding to respective sections as the predetermined section,
calculate the time-series data of the volume from the plurality of groups of two-dimensional ultrasonic image data, and
calculate the time-series data of the wall motion from the plurality of groups of two-dimensional ultrasonic image data.

5. The ultrasound diagnostic apparatus according to claim 4, wherein the processor is further configured to calculate time-series data obtained by averaging time-series data of wall motion for each of the plurality of groups of two-dimensional ultrasonic image data as the time-series data of the wall motion.

6. The ultrasound diagnostic apparatus according to claim 4, wherein the processor is further configured to:
  calculate a plurality of pieces of time-series data of wall motion corresponding to the plurality of groups of two-dimensional ultrasonic image data,
  calculate a plurality of pieces of second time-series data from the plurality of pieces of time-series data of the wall motion, and
  calculate an average of extremums in early diastole detected in each of the pieces of second time-series data as the second extremum.

7. The ultrasound diagnostic apparatus according to claim 1, wherein the processor is further configured to estimate a time phase of the early diastole in the first time-series data using a time phase in which the volume is minimum to detect the first extremum.

8. The ultrasound diagnostic apparatus according to claim 7, wherein the processor is further configured to estimate a time phase of the early diastole in the second time-series data using a time phase in which the first extremum has been detected to detect the second extremum.

9. The ultrasound diagnostic apparatus according to claim 1, wherein the processor is further configured to perform calculation processing of the volume using a result of tracking a position of the first region of interest by pattern matching between pieces of image data.

10. The ultrasound diagnostic apparatus according to claim 1, wherein the processor is further configured to perform calculation processing of the wall motion using a result of tracking a position of the second region of interest by pattern matching between pieces of image data.

11. The ultrasound diagnostic apparatus according to claim 1, wherein the processor is further configured to perform calculation processing of the volume using results of detecting a position of an inner cavity boundary as the first region of interest.

12. The ultrasound diagnostic apparatus according to claim 1, wherein the processor is further configured to perform calculation processing of the wall motion using results of detecting a position of an inner cavity boundary as the second region of interest.

13. The ultrasound diagnostic apparatus according to claim 1, wherein the processor is further configured to calculate at least one of strain and an area change ratio of a myocardium as the wall motion.

14. The ultrasound diagnostic apparatus according to claim 1, wherein the processor is further configured to calculate at least displacement as the wall motion.

15. The ultrasound diagnostic apparatus according to claim 1, wherein the processor is further configured to calculate wall motion of the entire left ventricle as the wall motion in the second region of interest.

16. The ultrasound diagnostic apparatus according to claim 1, wherein the processor is further configured to calculate wall motion of a valve ring of a left ventricle as the wall motion in the second region of interest.

17. The ultrasound diagnostic apparatus according to claim 1, wherein the processor is further configured to calculate at least one of a left ventricular ejection fraction and a cardiac mass from the time-series data of the volume.

18. The ultrasound diagnostic apparatus according to claim 1, wherein the index is indicative of a pressure of the left ventricle.

19. An image processing apparatus, comprising:
  a processor configured to:
    acquire a group of ultrasonic image data generated by ultrasonic scanning on a heart including at least a left ventricle for the period of one or more heart beats;
    calculate, from the group of the ultrasonic image data, time-series data of volume in a first region of interest in the left ventricle;
    calculate, from the group of the ultrasonic image data, time-series data of wall motion in a second region of interest in the left ventricle;
    calculate, from the time-series data of the volume, first time-series data that is time-series data of a time change rate of the volume;
    calculate, from the time series data of the wall motion, second time-series data that is time-series data of a time change rate of the wall motion;
    detect an extremum in early diastole of the first time-series data as a first extremum;
    detect an extremum in early diastole of the second time-series data as a second extremum; and
    calculate an index using the first extremum and the second extremum.

20. The image processing apparatus according to claim 19, wherein the index is indicative of a pressure of the left ventricle.

* * * * *